US011357969B2

(12) United States Patent
Peterson et al.

(10) Patent No.: US 11,357,969 B2
(45) Date of Patent: Jun. 14, 2022

(54) IMPLANTABLE STIMULATION NODE CONFIGURATION

(71) Applicant: Medtronic, Inc., Minneapolis, MN (US)

(72) Inventors: Erik J. Peterson, Fridley, MN (US); Mandla Thokozani Shongwe, Brooklyn Park, MN (US); Earle Timothy Roberts, Maple Grove, MN (US); David Andrew Dinsmoor, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 576 days.

(21) Appl. No.: 16/171,044

(22) Filed: Oct. 25, 2018

(65) Prior Publication Data

US 2020/0129752 A1    Apr. 30, 2020

(51) Int. Cl.
*A61N 1/02*    (2006.01)
*A61N 1/05*    (2006.01)
*A61N 1/372*   (2006.01)
*A61N 1/36*    (2006.01)

(52) U.S. Cl.
CPC .......... *A61N 1/025* (2013.01); *A61N 1/0551* (2013.01); *A61N 1/36139* (2013.01); *A61N 1/37217* (2013.01)

(58) Field of Classification Search
CPC .. A61N 1/025; A61N 1/0551; A61N 1/37217; A61N 1/36139; A61N 1/37252
See application file for complete search history.

(56) References Cited

U.S. PATENT DOCUMENTS

| | | | |
|---|---|---|---|
| 9,669,230 B2 * | 6/2017 | Koop | A61N 1/3925 |
| 2009/0264956 A1 * | 10/2009 | Rise | A61B 5/4836 607/45 |
| 2016/0331973 A1 * | 11/2016 | Wheeler | A61B 5/4836 |
| 2017/0080232 A1 * | 3/2017 | Torgerson | A61N 1/37247 |
| 2017/0173345 A1 * | 6/2017 | Abiri | A61N 1/3787 |
| 2017/0196457 A1 * | 7/2017 | Thakur | A61B 5/0205 |
| 2018/0178022 A1 * | 6/2018 | Koop | A61N 1/37276 |
| 2019/0015667 A1 * | 1/2019 | Taff | A61N 1/39622 |

* cited by examiner

*Primary Examiner* — Mallika D Fairchild
(74) *Attorney, Agent, or Firm* — Holland & Hart LLP

(57) ABSTRACT

Methods, systems, and devices for implantable node are described. The method may include storing, at an implantable stimulation node, a set of stimulation profiles in a memory during a configuration phase. The method may also include receiving a stimulation command corresponding to a stimulation profile of the set of stimulation profiles during a treatment phase. The method may further include delivering stimulation based at least in part on the stimulation profile corresponding to the received stimulation command. In some cases, the system may include an implantable hub, an implantable sensing node, and a sensing device.

18 Claims, 15 Drawing Sheets

IMPLANTABLE STIMULATION NODE CONFIGURATION

GOVERNMENT INTEREST

This invention was made with Government interest under prime award number N66001-15-C-4014, sub-award number RES509889 awarded by DARPA. The Government has certain rights in the invention.

BACKGROUND

The following relates generally to an implantable stimulation node, and more specifically to an implantable stimulation node data transfer configuration.

Stimulation therapy may use a device to apply an electric current to the body (e.g., nerve or muscle) to stimulate various tissue sites in the treatment of a variety of symptoms or conditions (e.g., chronic pain or tremor). The stimulation therapy device may be implanted in or external to the body, and the device may use one or more contacts (e.g., leads) that include electrodes to target treatment locations associated with the brain, the spinal cord, pelvic nerves, radial nerves, median nerves, ulnar nerves, and the like. In some cases, stimulation therapy devices may improve treatment targeting by increasing the number of electrical contacts with the body. Moreover, an increase in the number of electrical contacts may also reduce the side effects when delivering stimulation therapy.

A distributed implant approach may be taken to allow for more contacts with a greater reliability than non-distributed systems. A distributed system may communicate between devices to coordinate sensing and therapy delivery. Accordingly, as the number of distributed contacts increases, the data to be shared between the devices increases. The communication link between the devices may have a limited bandwidth and data transfer rate. Thus, communication between devices during an active mode (e.g., delivering stimulation in a time critical application) may be restricted.

SUMMARY

The described features generally relate to methods, systems, devices, or apparatuses that support an implantable stimulation node configuration. An implantable stimulation therapy system may reduce the amount of data that is communicated across the system by including some memory and processing power at each node (e.g., implanted stimulation node). The stimulation system may operate in a configuration phase where no therapy is being applied and the communication between devices is not time critical. The stimulation system may also operate in a treatment phase where therapy is being applied and the communication between devices is time critical. Thus, the amount of data that may need to be transmitted between therapy devices during time-critical applications (e.g., treatment phase where stimulation parameters should be quickly determined) may be reduced to accommodate the limited bandwidth and timing constraints.

In some cases, stimulation profiles that define a predetermined set of stimulation parameters may be stored and then used by therapy devices. By using prestored stimulation profiles, instead of having to send a full set of stimulation parameters across a bandwidth limited communication link, the system (e.g., a hub) can send an indication of which profile to use to a stimulation node. Thus, communication between the hub and stimulation node may operate effectively during time critical applications where large amounts of information (e.g., related to stimulation parameters) can be conveyed with reduced transmitted data (e.g., a profile indication).

The therapy system may also include sensing devices. For example, the sensing device may be a prosthetic, a wearable device, a therapy device, or the like. In some cases, profiles may exist for sensing parameters. The sensing profiles may be designed similarly to the stimulation profiles, such that communication between the sensing device and the hub may benefit from reduced transmitted data. In some examples, the profiles (e.g., stimulation or sensing) may define every parameter for operation or may define a portion of the parameters for operation. Accordingly, the system may provide a flexible communication configuration of reduced data based on the actual communication link restrictions (e.g., bandwidth or data rate) between devices of the therapy system.

A method of providing stimulation at an implantable stimulation node is described. The method may include storing a set of stimulation profiles in a memory during a configuration phase, receiving a stimulation command corresponding to a stimulation profile of the set of stimulation profiles during a treatment phase, and delivering stimulation based on the stimulation profile corresponding to the received stimulation command.

An apparatus for providing stimulation at an implantable stimulation node is described. The apparatus may include a processor, memory in electronic communication with the processor, and instructions stored in the memory. The instructions may be executable by the processor to cause the apparatus to store a set of stimulation profiles in a memory during a configuration phase, receive a stimulation command corresponding to a stimulation profile of the set of stimulation profiles during a treatment phase, and deliver stimulation based on the stimulation profile corresponding to the received stimulation command.

Another apparatus for providing stimulation at an implantable stimulation node is described. The apparatus may include means for storing a set of stimulation profiles in a memory during a configuration phase, receiving a stimulation command corresponding to a stimulation profile of the set of stimulation profiles during a treatment phase, and delivering stimulation based on the stimulation profile corresponding to the received stimulation command.

A non-transitory computer-readable medium storing code for providing stimulation at an implantable stimulation node is described. The code may include instructions executable by a processor to store a set of stimulation profiles in a memory during a configuration phase, receive a stimulation command corresponding to a stimulation profile of the set of stimulation profiles during a treatment phase, and deliver stimulation based on the stimulation profile corresponding to the received stimulation command.

Some examples of the method, apparatuses, and non-transitory computer-readable medium described herein may further include operations, features, means, or instructions for receiving an updated stimulation command during the treatment phase based on real-time sensed inputs, and delivering an updated stimulation within the treatment phase based on a stimulation profile corresponding to the updated stimulation command.

In some examples of the method, apparatuses, and non-transitory computer-readable medium described herein, the real-time sensed inputs change during the treatment phase.

Some examples of the method, apparatuses, and non-transitory computer-readable medium described herein may further include operations, features, means, or instructions for communicating signals over a limited bandwidth on communication circuitry, where the limited bandwidth may be based on the implantable stimulation node being implanted in a body.

In some examples of the method, apparatuses, and non-transitory computer-readable medium described herein, the set of stimulation profiles includes generic stimulation profiles and patient specific stimulation profiles.

In some examples of the method, apparatuses, and non-transitory computer-readable medium described herein, the configuration phase includes a first signal transmission timing restriction and the stimulation phase includes a second signal transmission timing restriction that may be greater than the first signal transmission timing restriction.

In some examples of the method, apparatuses, and non-transitory computer-readable medium described herein, the second signal transmission timing restriction may be based at least in part a feedback timing restriction corresponding to the delivered stimulation.

In some examples of the method, apparatuses, and non-transitory computer-readable medium described herein, the implantable stimulation node includes a set of electrodes.

In some examples of the method, apparatuses, and non-transitory computer-readable medium described herein, at least one electrode of the set of electrodes delivers stimulation according to the stimulation profile corresponding to the received stimulation command.

In some examples of the method, apparatuses, and non-transitory computer-readable medium described herein, the set of stimulation profiles include a lookup table, an algorithm that calculates modulation patterns from sensed inputs, or both.

Some examples of the method, apparatuses, and non-transitory computer-readable medium described herein may further include operations, features, means, or instructions for identifying a first set of stimulation parameters based on the stimulation profile corresponding to the received stimulation command, and identifying a second set of stimulation parameters directly from the received stimulation command, where the stimulation may be delivered based on the first set of stimulation parameters and the second set of stimulation parameters.

Some examples of the method, apparatuses, and non-transitory computer-readable medium described herein may further include operations, features, means, or instructions for identifying an index of the stimulation command, where the index may be associated with the stimulation profile of the set of stimulation profiles.

In some examples of the method, apparatuses, and non-transitory computer-readable medium described herein, the stimulation node may be configured to be implanted into a human body.

A method of providing stimulation at an implantable stimulation node is described. The method may include storing a set of stimulation profiles in a memory during a first time period, receiving a stimulation command from an implantable hub corresponding to a stimulation profile of the set of stimulation profiles during a second time period, and delivering stimulation based on the stimulation profile corresponding to the received stimulation command.

An apparatus for providing stimulation at an implantable stimulation node is described. The apparatus may include a processor, memory in electronic communication with the processor, and instructions stored in the memory. The instructions may be executable by the processor to cause the apparatus to store a set of stimulation profiles in a memory during a first time period, receive a stimulation command from an implantable hub corresponding to a stimulation profile of the set of stimulation profiles during a second time period, and deliver stimulation based on the stimulation profile corresponding to the received stimulation command.

Another apparatus for providing stimulation at an implantable stimulation node is described. The apparatus may include means for storing a set of stimulation profiles in a memory during a first time period, receiving a stimulation command from an implantable hub corresponding to a stimulation profile of the set of stimulation profiles during a second time period, and delivering stimulation based on the stimulation profile corresponding to the received stimulation command.

A non-transitory computer-readable medium storing code for providing stimulation at an implantable stimulation node is described. The code may include instructions executable by a processor to store a set of stimulation profiles in a memory during a first time period, receive a stimulation command from an implantable hub corresponding to a stimulation profile of the set of stimulation profiles during a second time period, and deliver stimulation based on the stimulation profile corresponding to the received stimulation command.

Some examples of the method, apparatuses, and non-transitory computer-readable medium described herein may further include operations, features, means, or instructions for detecting, by a sensing device, real-time sensed inputs, and transmitting, by the sensing device, the real-time sensed inputs to the implantable hub, where the sensing device may be configured to be coupled with a human body.

Some examples of the method, apparatuses, and non-transitory computer-readable medium described herein may further include operations, features, means, or instructions for determining, at the implantable hub, the stimulation command corresponding to the stimulation profile based on the real-time sensed inputs received from the sensing device, and transmitting the stimulation command to one or more of the set of implantable stimulation nodes.

In some examples of the method, apparatuses, and non-transitory computer-readable medium described herein, the sensing device includes a prosthetic, a wearable device, a therapy device, or a combination thereof.

In some examples of the method, apparatuses, and non-transitory computer-readable medium described herein, the implantable hub includes a battery source configured to provide power to the set of implantable stimulation nodes.

In some examples of the method, apparatuses, and non-transitory computer-readable medium described herein, the implantable hub may be configured to wirelessly communicate with an external device.

In some examples of the method, apparatuses, and non-transitory computer-readable medium described herein, the implantable hub may be electrically coupled with the set of implantable stimulation nodes via a wired connection.

A method of electrical sensing at an implantable electrical sensing device is described. The method may include receiving configuration instructions during a configuration phase, storing a set of sensing profiles in a memory based on the received configuration instructions, where each sensing profile of the set of sensing profiles defines a set of data processing parameters, receiving a sensed input during a sensing phase, and transmitting a reduced set of the received sensed input based on the set of data processing parameters corresponding to a sensing profile of the set of sensing profiles.

An apparatus for electrical sensing at an implantable electrical sensing device is described. The apparatus may include a processor, memory in electronic communication with the processor, and instructions stored in the memory. The instructions may be executable by the processor to cause the apparatus to receive configuration instructions during a configuration phase, store a set of sensing profiles in a memory based on the received configuration instructions, where each sensing profile of the set of sensing profiles defines a set of data processing parameters, receive a sensed input during a sensing phase, and transmit a reduced set of the received sensed input based on the set of data processing parameters corresponding to a sensing profile of the set of sensing profiles.

Another apparatus for electrical sensing at an implantable electrical sensing device is described. The apparatus may include means for receiving configuration instructions during a configuration phase, storing a set of sensing profiles in a memory based on the received configuration instructions, where each sensing profile of the set of sensing profiles defines a set of data processing parameters, receiving a sensed input during a sensing phase, and transmitting a reduced set of the received sensed input based on the set of data processing parameters corresponding to a sensing profile of the set of sensing profiles.

A non-transitory computer-readable medium storing code for electrical sensing at an implantable electrical sensing device is described. The code may include instructions executable by a processor to receive configuration instructions during a configuration phase, store a set of sensing profiles in a memory based on the received configuration instructions, where each sensing profile of the set of sensing profiles defines a set of data processing parameters, receive a sensed input during a sensing phase, and transmit a reduced set of the received sensed input based on the set of data processing parameters corresponding to a sensing profile of the set of sensing profiles.

Some examples of the method, apparatuses, and non-transitory computer-readable medium described herein may further include operations, features, means, or instructions for reducing the received sensed input to the reduced set of the received sensed input by applying the set of data processing parameters corresponding to the sensing profile of the set of sensing profiles.

In some examples of the method, apparatuses, and non-transitory computer-readable medium described herein, the reducing may be based on an available bandwidth, a timing constraint, a pre-configuration, or a combination thereof.

DETAILED DESCRIPTION

Figure 1:
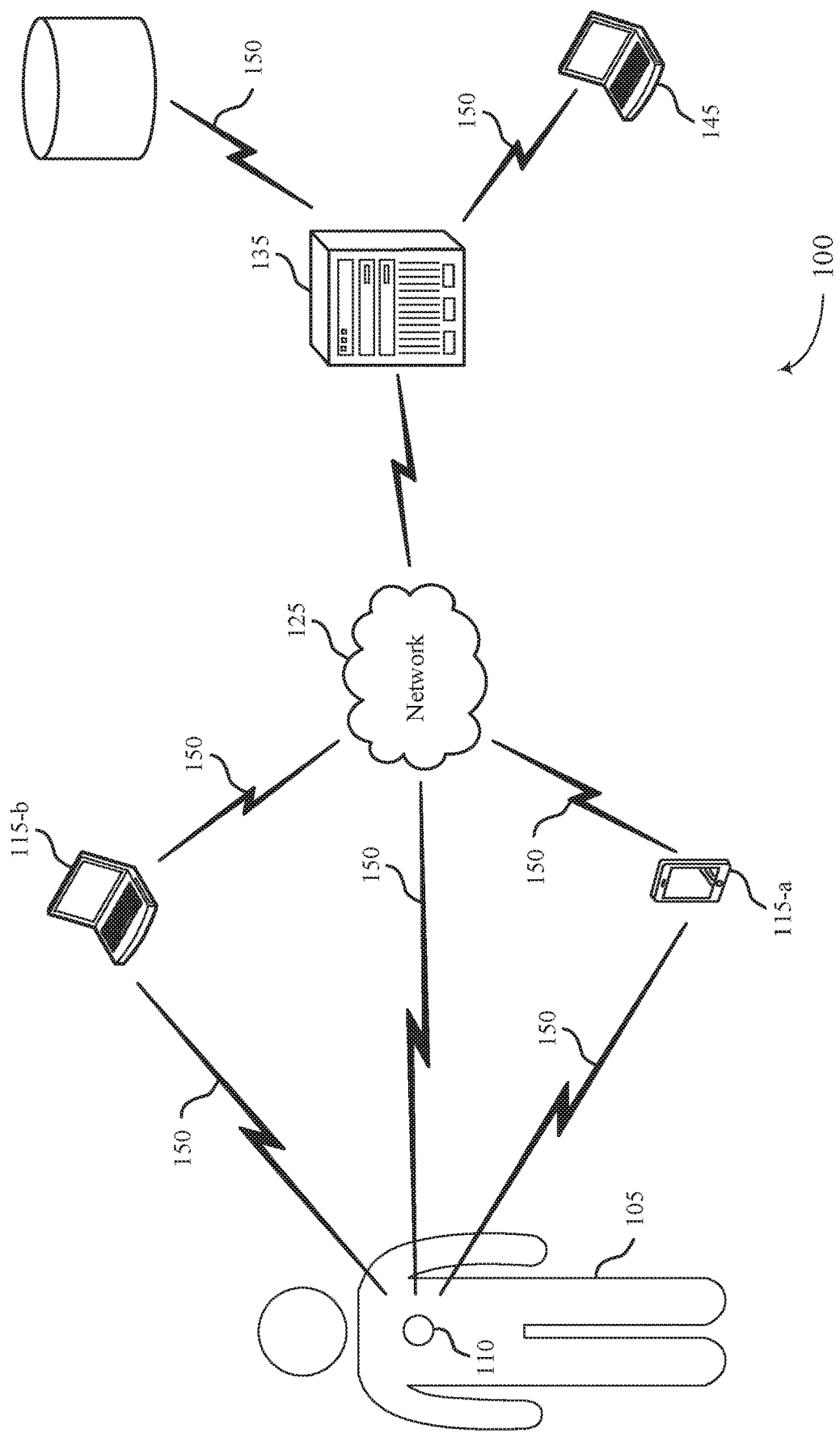
FIG. 1 illustrates an example of a system for implantable nodes that supports implantable stimulation node configuration in accordance with aspects of the present disclosure.

The present disclosure describes devices, systems, and methods for an improved stimulation system for delivering electrical stimulation to a body. The stimulation system allows for efficient operation during time-critical applications when large amounts of information may need to be communicated between devices of the system quickly (e.g., between a hub and stimulation nodes in a distributed implant stimulation system). In some cases, the communication link between the devices may have a limited bandwidth and data transfer rate due to hardware restrictions or other characteristics associated with being implanted in a body. Thus, communication between devices during an active mode (e.g., delivering stimulation in a time-critical application) may be restricted (e.g., bandwidth or data rate). Moreover, in distributed systems with several nodes communicating and sharing power, the amount of data to be transmitted across the system can be large. In accordance with aspects of the present disclosure, the system may convey large amounts of information between devices using a reduced amount of actual transmitted data, for example through use of stored stimulation profiles on the stimulation nodes themselves. Thus, devices may efficiently operate during time-critical applications to satisfy restricted bandwidth and data transfer rates.

For example, an implantable stimulation therapy system may communicate with limited transmitted data by including some memory and processing power at each node (e.g., implanted stimulation node). The stimulation system may operate in a configuration phase when no stimulation therapy is applied and the communication between devices is not time critical. The configuration phase may be prior to implantation of the device, or the configuration phase may be after implantation but during a non-treatment time (e.g., between treatments). The stimulation system may also operate in a treatment phase when therapy is applied and the communication between devices is time critical.

In some cases, stimulation profiles may be used by therapy devices to define a predetermined set of stimulation parameters. That is, instead of sending the full set of detailed stimulation parameters, an indication of which profile to be used may be sent to a stimulation node. Additionally, the stimulation profiles may be stored in a memory of the stimulation node and a hub. Thus, communication between the hub and stimulation node may operate effectively at time critical applications where large amounts of information (e.g., related to stimulation parameters) can be conveyed with reduced transmitted data (e.g., a profile indication). In some examples, a look up table or algorithm may be used as the indication of which profile to be used for stimulation. Further, the stimulation profile used by a stimulation node may be changed during an active phase. For example, a sensed input may correlate to a new set of stimulation parameters that are indicated by a different stimulation profile. The hub may transmit an indication of the updated profile to update the operating parameters of the stimulation node. In some cases, the stimulation node may include a set of electrodes that deliver the current to the tissue. The set of electrodes may operate according to the defined parameters of an indicated stimulation profile.

The therapy system may also include sensing devices. For example, the sensing device may be a prosthetic, a wearable device, a therapy device, or the like. In some cases, profiles may exist for sensing parameters. The sensing profiles may be designed similarly to the stimulation profiles, such that communication between the sensing device and the hub may benefit from reduced transmitted data. For example, a sensing profile may define one or more data processing parameters, that when implemented by the sensing device, reduces the amount of data transmitted from the sensing device to a hub or elsewhere in the system. In some examples, a look up table or algorithm may be used as an indication of which profile correlates to the sensed inputs.

In some examples, the profiles (e.g., stimulation or sensing) may define every parameter for operation (e.g., the full set) or may define a portion of the parameters for operation (e.g., a subset of the parameters). The split between how many of the parameters are stored in the profile versus how many are transmitted in real time may be dynamically determined by the system based on the current availability of resources (e.g., bandwidth and timing constraints). Accordingly, the system may provide a flexible communication configuration of reduced data based on the actual communication link restrictions (e.g., bandwidth or data rate) between devices of the therapy system.

Aspects of the disclosure are initially described in the context of a wireless patient monitoring system, which may include medical devices configured to deliver stimulation therapy. Aspects of the disclosure are further illustrated by and described with reference to apparatus diagrams, system diagrams, and flowcharts that relate to implantable stimulation node configuration.

FIG. 1 illustrates an example of a wireless patient monitoring system 100 in accordance with various aspects of the present disclosure. The wireless patient monitoring system 100 may include a patient 105 wearing, carrying, or otherwise coupled with a medical device 110. Although a single medical device 110 is shown, multiple medical devices 110 may be coupled to the patient 105. The patient 105 may be a patient in a hospital, nursing home, home care, a medical facility, or another care facility. The medical device 110 may transmit signals via wireless communications links 150 to computing devices 115 or to a network 125.

The medical device 110 may include one or more sensors configured to collect a variety of physiological parameters as well as information related to the location and movement of the patient 105. For example, the medical device 110 may include a pulse oximetry (SpO2) sensor, a capnography sensor, a heart rate sensor, a blood pressure sensor, an electrocardiogram (ECG) sensor, a respiratory rate sensor, a glucose level sensor, a depth of consciousness sensor, a body temperature sensor, an accelerometer, a global positioning sensor, a sensor which triangulates position from multiple local computing devices 115, or any other sensor configured to collect physiological, location, or motion data associated with the patient 105.

The medical device 110 may be coupled with the patient 105 in a variety of ways depending on the data being collected. For example, the medical device 110 may be directly coupled with the patient 105 (e.g., physically connected to the patient's chest, worn around the patient's wrist, attached to the patient's finger, or positioned over the patients nose or mouth). The data collected by the medical device 110 may be wirelessly transmitted to either the computing devices 115 or to the remote computing device 145 (via the network 125 and central station 135). Data transmission may occur via, for example, frequencies appropriate for a personal area network (such as Bluetooth, Bluetooth Low Energy (BLE), or IR communications) or local (e.g., wireless local area network (WLAN)) or wide area network (WAN) frequencies such as radio frequencies specified by IEEE standards (e.g., IEEE 802.15.4 standard, IEEE 802.11 standard (Wi-Fi), IEEE 802.16 standard (WiMAX), etc.).

Computing device 115-a may be a wireless device such as a tablet, cellular phone, personal digital assistant (PDA), a dedicated receiver, or other similar device or a spatially distributed network of devices configured to receive signals from the medical device 110. Computing device 115-b may be a wireless laptop computer, a clinician Workstation on Wheels, or a smart hospital bed configured to receive signals from the medical device 110. The computing devices 115 may be in communication with a central station 135 via network 125.

The medical device 110 may also communicate directly with the central station 135 via the network 125. The central station 135 may be a server or a central nurse station located within the hospital or in a remote location. The central station 135 may be in further communication with one or more remote computing devices 145, thereby allowing a clinician to remotely monitor the patient 105. The central station 135 may also be in communication with various remote databases 140 where the collected patient data may be stored. In some cases, the remote databases 140 include electronic medical records (EMR) applications for storing and sharing patient data.

In accordance with various aspects of the present disclosure, methods and apparatuses are described for an implantable stimulation node configuration. Medical device 110 may be an example of a stimulation therapy system. Medical device 110 may include a one or more stimulation nodes, a hub, and one or more sensing nodes. A clinician may select values for a number of programmable stimulation profiles and sensing profiles to define the electrical stimulation therapy to be delivered by the implantable stimulator to the patient 105 based on the sensed inputs at a sensing node or device. For example, the clinician may identify in a profile one or more electrodes, a polarity of each selected electrode, a voltage or current amplitude, a pulse width, and a pulse frequency as stimulation parameters. The clinician may program the medical device 110 with one or more stimulation profiles and/or sensing profiles during a configuration phase using a computing device 115.

Conventionally, a stimulation node may not have had the ability to store or process stimulation profiles. As such, conventional stimulation systems may have required that all of the treatment or sensing parameters be transmitted between the hub and the stimulation or sensing nodes in real time. In distributed systems with multiple stimulation nodes communicating with each other and with a central hub, the amount of data being transmitted across the system may be sizable. Moreover, implantable stimulation systems may operate with a limited bandwidth or data rate due to the nature and hardware restrictions associated with being implanted within a human body. Therefore, the amount of data to be sent during time-critical applications may exceed the bandwidth or data rate limitations of some distributed stimulation systems. Aspects of the present disclosure provide examples of a stimulation or sensing node that is capable of storing and processing indications of stimulation profiles, which can reduce the actual amount of data being transmitted across the system while conveying the same amount of information.

For example, during a treatment phase, the stimulation node and hub of medical device 110 may communicate using stored stimulation profiles. For example, the hub may transmit a small amount of data, which indicates the stimulation profile to be used by the stimulation node (e.g., the electrodes of the stimulation node). The indication may not contain the details of each stimulation parameter, but instead, the indication may include an algorithm or index corresponding to a look up table that identifies a stimulation profile that is stored on the stimulation node. Thus, the stimulation profile may include the detailed parameters and a reduced amount of data may allow for efficient identification of detailed operating parameters. In some cases, it may be necessary to transmit reduced data due to bandwidth and/or data rate restrictions. For example, in time-critical applications when a set of stimulation parameters may need to be quickly conveyed to a stimulation node, the system may use the available bandwidth to send an indication that identifies the stimulation parameters rather than waiting until sufficient bandwidth is available to transmit the full set of stimulation parameters. Accordingly, the use of prestored profiles provide the advantage of reducing the amount of data to be transmitted between devices for operation.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
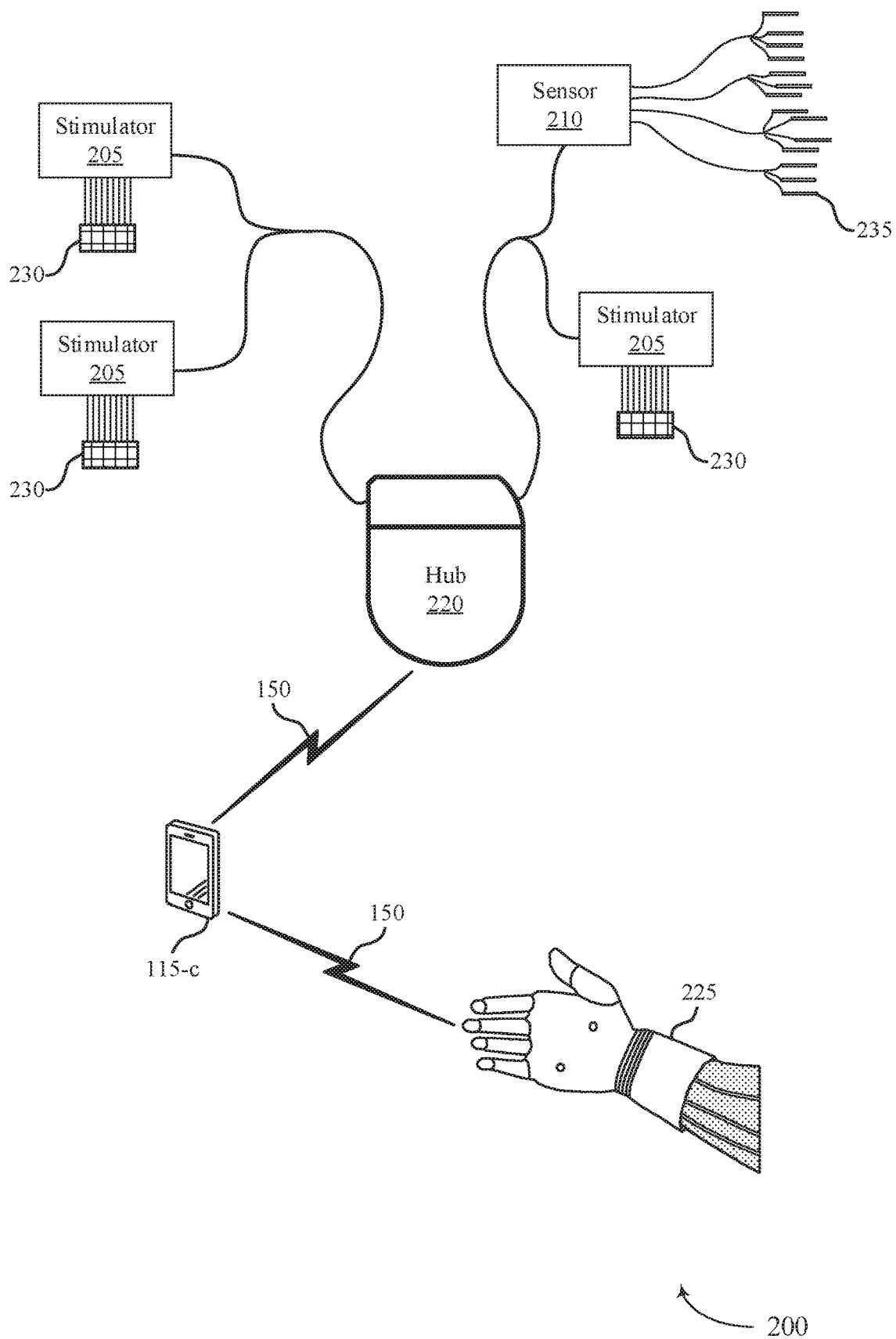
FIG. 2 illustrates an example of a system that supports implantable stimulation node configuration in accordance with aspects of the present disclosure.

FIG. 2 illustrates an example of a system 200 that supports implantable stimulation node configuration in accordance with aspects of the present disclosure. In some examples, system 200 may implement aspects of wireless communication system 100 and may include one or more stimulation nodes 205, one or more sensing nodes 210, a computing device 115-c, a hub 220, and a sensing device 225. System 200 may be an example of a closed-loop therapy system.

Stimulation node 205 may include electrode contacts 230 that deliver stimulation to tissue (e.g., the radial nerve, median nerve, or ulnar nerve). In some examples, each stimulation node 205 may include 32 electrode contacts 230. More or fewer electrode contacts 230 may be present to deliver stimulation to the tissue. Stimulation node 205 may be connected to hub 220 via a wired lead. The wired lead may support a limited bandwidth or data rate due to the material or size of the lead, or other characteristics associated with being implanted in a body. In some cases, stimulation node 205 is a part of closed-loop system 200 that allows real-time updates to stimulation outputs based on real-time sensed inputs. For example, updates may happen periodically (e.g., every 10 milliseconds), which may allow the therapy system 200 to act as a real time streaming neural stimulation system by adapting therapy parameters quickly.

As discussed herein, a stimulation node 205 may have stimulation profiles prestored before providing treatment. In a configuration phase, the memory of the stimulation node 205 may store various combinations of stimulation parameters in one or more stimulation profiles. In some cases, the stimulation profiles may define the electrode contact 230 for treatment, maximum and minimum, amplitude of current to be delivered, timing of delivered pulses, inter-pulse interval, and the like. Therefore, a stimulation profile may define some or all of the parameters needed for the stimulation node 205 to delivery treatment. A preloaded algorithm may define how the stimulation profile is to be modulated in time (e.g., according to a sine wave or sawtooth profile) during the treatment phase, if modulated at all. The various stimulation parameters may be unique to each electrode contact 230 of each stimulation node 205. Thus, the adaptability of the stimulation parameters provides for specific targeted therapy. In some examples, the stimulation profiles may define parameters for each pulse of each electrode contact 230, and each pulse for each electrode contact 230 may be unique. Stimulation node 205 may include a stimulation engine or other power source to generate the electric current to be delivered to the tissue.

In some cases, the stimulation node 205 may include a processor (e.g., a microprocessor). Further, the processing power of each stimulation node's 205 processor may be based on the tissue the electrode contacts 230 are connected to (e.g., nerve type). The presence of processing power at the stimulation node 205 allows a reduced set of commands to be transmitted for updating stimulation parameters. The reduced set of commands includes the indication of what stimulation profile to use. For example, an index may be received at the stimulation node 205 that corresponds to a first stimulation profile based on a look up table stored in the memory of the stimulation node 205.

Sensing node 210 may be connected to the hub 220 via leads, and sensing node 210 may include electrodes 235 that act as biopotential amplifiers to pick up electromyogram (EMG) signals from the muscles (e.g., muscles in the arm). In some examples a 16 channel EMG is used to collected information from the muscles. This information may act as an input to determine stimulation parameters for stimulation node 205 or motor control of an external device (e.g., sensing device 225). The sensing node 210 may be distributed away from the stimulation node 205 such that sensing node 210 may measure inputs at one part of the body (e.g., the leg), and the stimulation node 205 may provide therapy based on the inputs at a different part of the body (e.g., the back).

In some examples, sensing node 210 may include a processor and memory and may be preloaded with sensing profiles, which define a set of sensed parameters. For example, a sensing profile may define a range of the size and shape of a measured waveform for an EMG signal. The sensing profiles may be similarly designed to the stimulation profiles (e.g., profiles may allow for indications of reduced data corresponding to each profile to be used in communication with the hub 220).

Hub 220 may be an implantable neural controller (INC) and may provide power to the stimulation node 205 and sensing node 210. Power and data may be transmitted between hub 220, stimulation nodes 205, and sensing nodes 210 via implantable wire leads. Hub 220 may have stimulation profiles and sensing profiles prestored in a memory during a configuration phase. The stimulation profiles allow the hub 220 to communicate with stimulation node 205 using a reduced amount of transmitted data. The sensing profiles may allow the hub 220 to communicate with sensing node 210 using a reduced amount of transmitted data. The hub 220 may include a processor that allows for a determination of which stimulation profiles to use for specific sensing profiles. The signaling between the hub 220, stimulation nodes 205, and sensing nodes 210 may create a closed-loop system that rapidly updates stimulation therapy parameters based on live streaming inputs.

In some cases, hub 220 may communicate wirelessly with an external computing device 115-c (e.g., via Bluetooth). Computing device 115-c may be a smart device that provides a communication interface between hub 220 and sensing device 225. Computing device 115-c may receive motor control information from the hub 220 (e.g., based on sensed inputs at the sensing node 210) and transfer the motor control information to sensing device 225 (e.g., a prosthetic hand). In some cases, computing device 115-c may communicate wirelessly with sensing device 225.

Sensing device 225 may receive operation instructions (e.g., motor control instructions) from computing device 115-c. Accordingly, sensing device 225 may execute the received operation instructions. In some examples, sensing device 225 may include a sensor that receives sensed inputs, such as heart rate or a tactile experiences. Sensing device 225 may transmit this sensor data back to hub 220, via computing device 115-c. In some cases, the sensor data may determine a stimulation therapy that is delivered at stimulation node 205. In some examples, the sensing device 225 may be a prosthetic, a wearable monitoring device, or the like.

Figure 3:
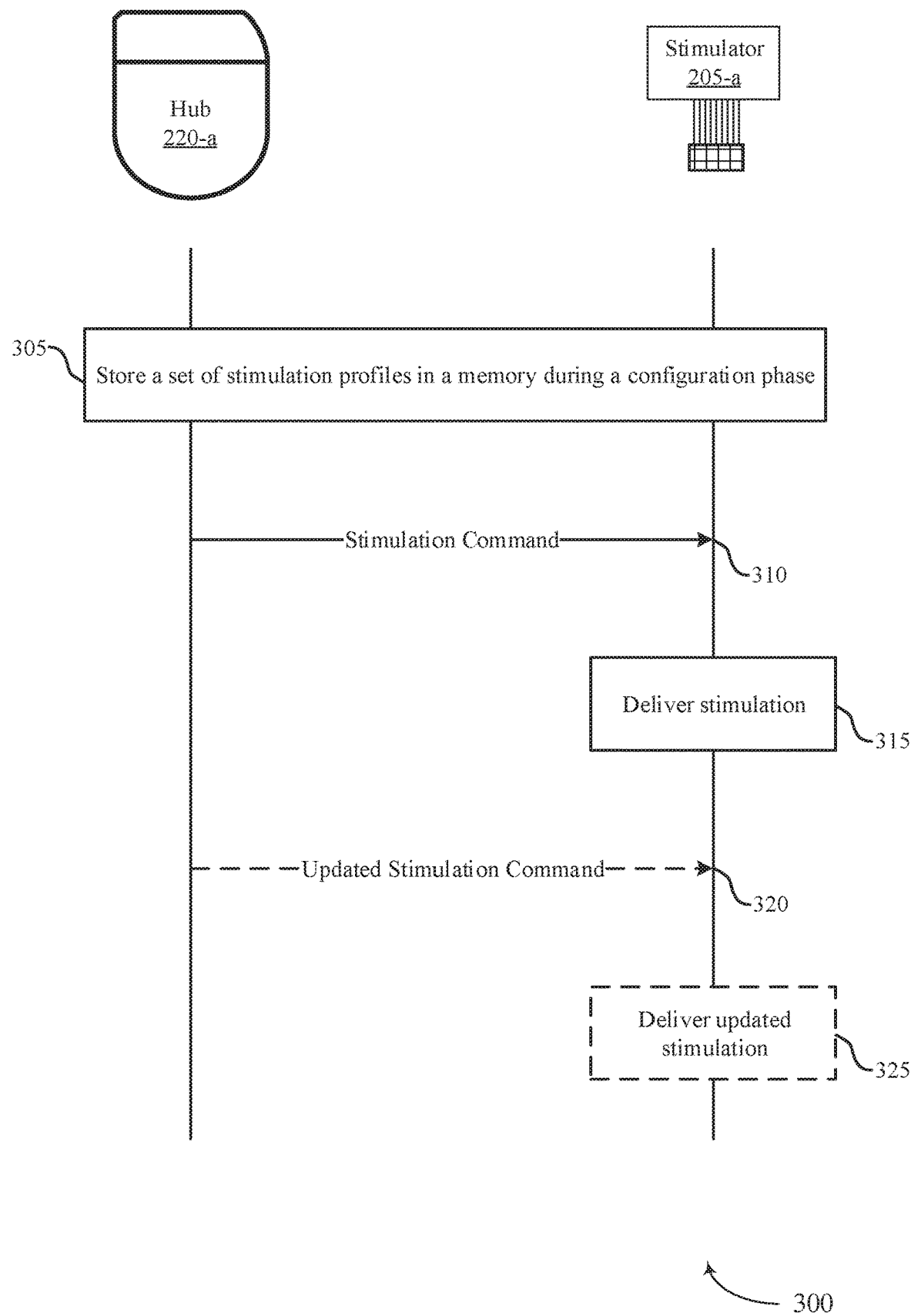
FIG. 3 illustrates an example of a process flow that supports implantable stimulation node configuration in accordance with aspects of the present disclosure.

FIG. 3 illustrates an example of a process flow 300 that supports implantable stimulation node configuration in accordance with aspects of the present disclosure. In some examples, process flow 300 may implement aspects of wireless communication system 100 and may include hub 220-a and stimulation node 205-a, which may be respective examples of hub 220 and stimulation node 205 as described with reference to FIG. 2. Alternative examples of the following may be implemented, where some steps are performed in a different order or not at all. Some steps may additionally include additional features not mentioned above.

At 305, hub 220-a and stimulator node 205-a may store a set of stimulation profiles in a memory of each device during a configuration phase. For example, the configuration phase may occur before implantation of the devices. In other examples, the hub 220-a and stimulator 205-a may be configured after implanted in the device. Hub 220-a and stimulation node 205-a may also store algorithms and look up tables corresponding to the stimulation profiles.

At 310, stimulation node 205-a may receive from hub 220-a a stimulation command corresponding to a stimulation profile of the set of stimulation profiles. The stimulation command may be received during a treatment phase. The stimulation command may indicate (e.g., via an index) which stimulation profile and algorithm to use at stimulation node 205-a during treatment. Thus, the stimulation node 205-a may process the command to determine the corresponding profile that defines the stimulation parameters. For example, the indication may include an index, and the stimulation node 205-a may look up in a look-up table the index to determine the corresponding stimulation profile.

At 315, stimulation node 205-a may deliver stimulation to a patient based on the stimulation profile indicated in the received stimulation command. In some cases, the stimulation profiles may define the electrode for treatment, maximum and minimum, amplitude of current to be delivered, timing of delivered pulses, inter-pulse interval, and the like. A preloaded algorithm may define how the stimulation profile is to be modulated in time (e.g., according to a sine wave or sawtooth profile) during the treatment phase, if modulated at all. The various stimulation parameters may be unique to each electrode contact of each stimulation node 205-a.

At 320, stimulation node 205-a may receive, from hub 220-a, an updated stimulation command corresponding to a stimulation profile of the set of stimulation profiles. The stimulation profile may be the same or different from the first stimulation profile received at 310. In some cases, the updated stimulation command may be a result of new sensed inputs from a sensing node or sensing device. At 325, stimulation node 205-a may deliver stimulation to a patient based on an updated stimulation profile indicated in the received updated stimulation command.

Figure 4:
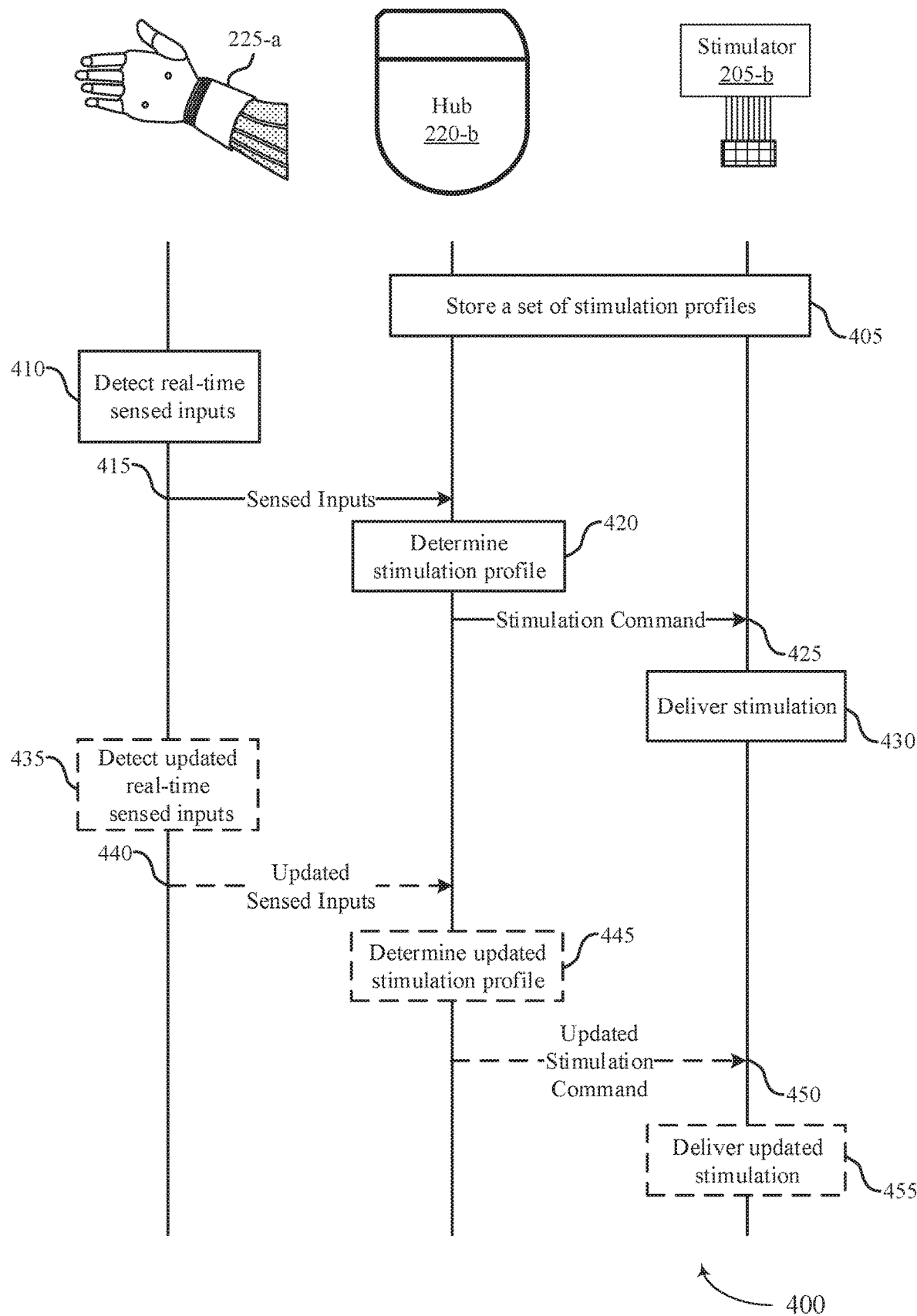
FIG. 4 illustrates an example of a process flow that supports implantable stimulation node configuration in accordance with aspects of the present disclosure.

FIG. 4 illustrates an example of a process flow 400 that supports implantable stimulation node configuration in accordance with aspects of the present disclosure. In some examples, process flow 400 may implement aspects of wireless communication system 100 and may include sensing device 225-a, hub 220-b, and stimulation node 205-b, which may be respective examples of sensing device 225, hub 220, and stimulation node 205 as described with reference to FIGS. 2 and 3. Alternative examples of the following may be implemented, where some steps are performed in a different order or not at all. Some steps may additionally include additional features not mentioned above.

At 405, hub 220-b and stimulation node 205-b may store a set of stimulation profiles in a memory of each device during a configuration phase. For example, the configuration phase may occur before implantation of the devices or after implantation but during a time that is not designated for treatment. Hub 220-b and stimulation node 205-b may also store algorithms and look up tables corresponding to the stimulation profiles.

At 410, sensing device 225-a may detect real-time sensed inputs (e.g., touching an object). At 415, hub 220-b may receive the sensed inputs from the sensing device 225-a. For example, the sensed inputs may be received via a wireless or wired communication link. The sensed inputs may be received after a very short time (e.g., 10 milliseconds) such that the system operates in real time or near real time.

At 420, hub 220-b may use the received sensed inputs to determine a stimulation profile (e.g., determine which nerve should be stimulated to identify the presence of the object). Once the stimulation profile is determined, a corresponding indication may be determined at hub 220-b.

At 425, stimulation node 205-b may receive, from hub 220-b, a stimulation command corresponding to a stimulation profile of the set of stimulation profiles. The stimulation command may be received during a treatment phase. The stimulation command may indicate (e.g., via an index) what stimulation profile and algorithm to use at stimulation node 205-b during treatment. Thus, the stimulation node 205-b may process the command to determine the corresponding profile that defines the stimulation parameters. For example, the indication may include an index, and the stimulation node 205-b may look up in a look-up table the index to determine the corresponding stimulation profile.

At 430, stimulation node 205-b may deliver stimulation to a patient based on the stimulation profile indicated in the received stimulation command. In some cases, the stimulation profiles may define the electrode for treatment, maximum and minimum, amplitude of current to be delivered, timing of delivered pulses, inter-pulse interval, and the like. A preloaded algorithm may define how the stimulation profile is to be modulated in time (e.g., according to a sine wave or sawtooth profile) during the treatment phase, if modulated at all. The various stimulation parameters may be unique to each electrode contact of each stimulation node 205-b.

At 435, sensing device 225-a may detect updated real-time sensed inputs (e.g., touching a different side of the object). Optionally at 440, hub 220-b may receive the updated sensed inputs from the sensing device 225-a. For example, the updated sensed inputs may be received via a wireless or wired communication link. The updated sensed inputs may be received after a very short time (e.g., 10 milliseconds) such that the system operates in real time. In some cases, the sensed inputs may be unsolicited or independent from a request. The communication between the hub 220-b and sensing device 225-a may be synchronized with the real-time reporting of the sensed inputs, for example, when the data reporting uses a relatively high bandwidth. Thus, this synchronization may result in maximizing channel bandwidth utilization.

At 445, hub 220-b may use the received updated sensed inputs to determine an updated stimulation profile (e.g., determine which nerve should be stimulated to identify the presence of the object). Once the updated stimulation profile is determined, a corresponding indication may be determined at hub 220-b.

At 450, stimulation node 205-b may receive, from hub 220-b, an updated stimulation command corresponding to a new stimulation profile of the set of stimulation profiles. The updated stimulation command may be received during a treatment phase. The updated stimulation command may indicate (e.g., via an index) what stimulation profile and algorithm to use at stimulation node 205-b during treatment. Thus, the stimulation node 205-b may process the command to determine the corresponding profile that defines the updated stimulation parameters. For example, the indication may include an index, and the stimulation node 205-b may look up in a look up table the index to determine the corresponding stimulation profile. At 455, stimulation node 205-b may deliver stimulation to a patient based on the updated stimulation profile indicated in the received updated stimulation command.

Figure 5:
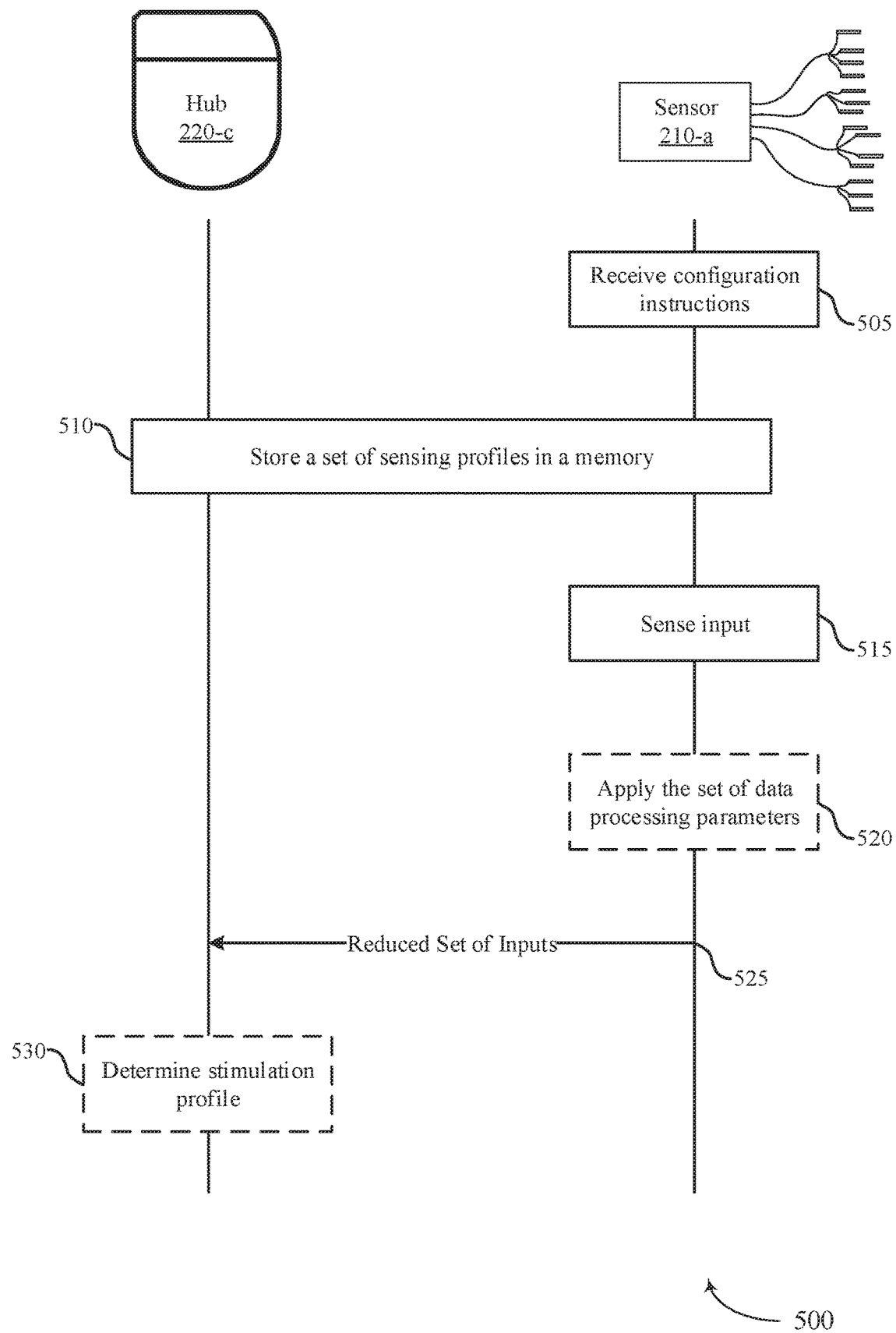
FIG. 5 illustrates an example of a process flow that supports implantable stimulation node configuration in accordance with aspects of the present disclosure.

FIG. 5 illustrates an example of a process flow 500 that supports implantable stimulation node configuration in accordance with aspects of the present disclosure. In some examples, process flow 500 may implement aspects of wireless communication system 100 and may include sensing node 210-a and hub 220-c, which may be respective examples of sensing node 210 and hub 220 as described with reference to FIGS. 2, 3, and 4. Alternative examples of the following may be implemented, where some steps are performed in a different order or not at all. Some steps may additionally include additional features not mentioned above.

At 505, sensing node 210-a may receive configuration instructions during a configuration phase. For example, the configuration phase may occur before implantation of the devices or after implantation but during a non-treatment phase.

At 510, hub 220-c and sensing node 210-a may store a set of sensing profiles based at least in part on the received configuration instructions, where each sensing profile of the set of sensing profiles defines a set of data processing parameters for sensed inputs at sensing node 210-a. Hub 220-c and sensing node 210-a may also store algorithms and look up tables corresponding to the sensing profiles.

At 515, sensing node 210-a may receive a sensed input during a sensing phase (e.g., time-critical treatment phase). The sensed input may include an EMG signal. At 520, sensing node 210-a may reduce the received sensed input to a reduced set of the received sensed input by applying the set of data processing parameters corresponding to the sensing profile of the set of sensing profiles. In some cases, the reduction may be based on one or more of an available bandwidth, a timing constraint, a pre-configuration, or a combination thereof.

At 525, hub 220-c may receive, from sensing node 210-a via a wired connection, a reduced set of the received sensed inputs based at least in part on the set of data processing parameters corresponding to a sensing profile of the set of sensing profiles. The received sensed inputs may be received during a treatment phase. The received sensed input may indicate (e.g., via an index) a sensing profile. At 530, hub 220-c may determine a stimulation profile based on the received sensed inputs.

Figure 6:
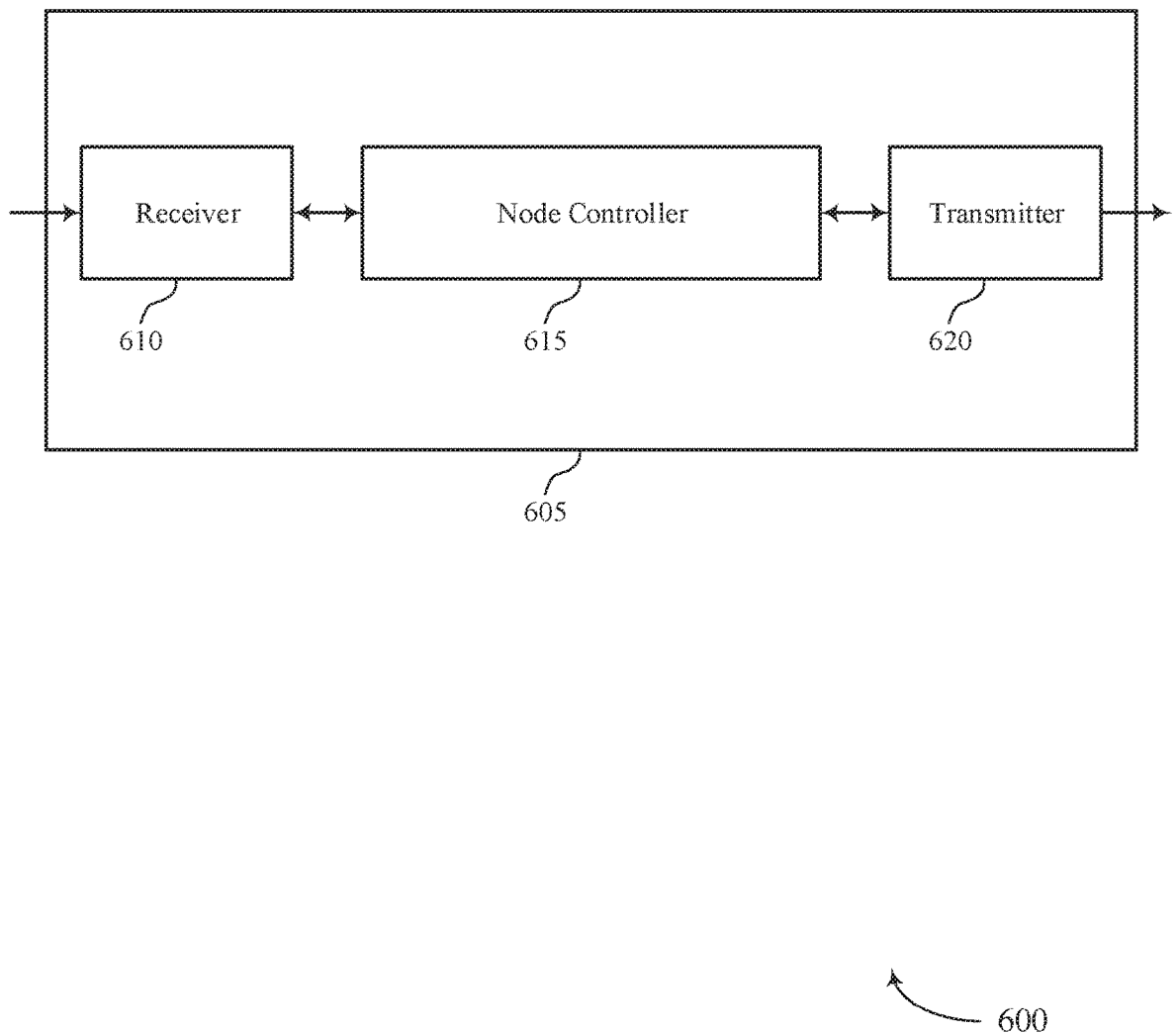
FIGS. 6 and 7 show block diagrams of devices that support implantable stimulation node configuration in accordance with aspects of the present disclosure.

FIG. 6 shows a block diagram 600 of a device 605 that supports implantable stimulation node configuration in accordance with aspects of the present disclosure. The device 605 may be an example of aspects of a device as described herein. The device 605 may include a receiver 610, a node controller 615, and a transmitter 620. The device 605 may also include a processor. Each of these components may be in communication with one another (e.g., via one or more buses).

The receiver 610 may receive information such as packets, user data, or control information associated with various information channels (e.g., control channels, data channels, and information related to implantable stimulation node configuration, etc.). Information may be passed on to other components of the device 605. The receiver 610 may be an example of aspects of the transceiver 920 described with reference to FIG. 9. The receiver 610 may utilize a single antenna or a set of antennas.

The node controller 615 may store a set of stimulation profiles in a memory during a configuration phase, receive a stimulation command corresponding to a stimulation profile of the set of stimulation profiles during a treatment phase, and deliver stimulation based on the stimulation profile corresponding to the received stimulation command. The node controller 615 may also store a set of stimulation profiles in a memory during a first time period, receive a stimulation command from an implantable hub corresponding to a stimulation profile of the set of stimulation profiles during a second time period, and deliver stimulation based on the stimulation profile corresponding to the received stimulation command. The node controller 615 may also receive configuration instructions during a configuration phase, store a set of sensing profiles in a memory based on the received configuration instructions, where each sensing profile of the set of sensing profiles defines a set of data processing parameters, receive a sensed input during a sensing phase, and transmit a reduced set of the received sensed input based on the set of data processing parameters corresponding to a sensing profile of the set of sensing profiles. The node controller 615 may be an example of aspects of the node controller 910 described herein.

The node controller 615, or its sub-components, may be implemented in hardware, code (e.g., software or firmware) executed by a processor, or any combination thereof. If implemented in code executed by a processor, the functions of the node controller 615, or its sub-components may be executed by a general-purpose processor, a DSP, an application-specific integrated circuit (ASIC), a FPGA or other programmable logic device, discrete gate or transistor logic, discrete hardware components, or any combination thereof designed to perform the functions described in the present disclosure.

The node controller 615, or its sub-components, may be physically located at various positions, including being distributed such that portions of functions are implemented at different physical locations by one or more physical components. In some examples, the node controller 615, or its sub-components, may be a separate and distinct component in accordance with various aspects of the present disclosure. In some examples, the node controller 615, or its sub-components, may be combined with one or more other hardware components, including but not limited to an input/output (I/O) component, a transceiver, a network server, another computing device, one or more other components described in the present disclosure, or a combination thereof in accordance with various aspects of the present disclosure.

The transmitter 620 may transmit signals generated by other components of the device 605. In some examples, the transmitter 620 may be collocated with a receiver 610 in a transceiver module. For example, the transmitter 620 may be an example of aspects of the transceiver 920 described with reference to FIG. 9. The transmitter 620 may utilize a single antenna or a set of antennas.

Figure 7:
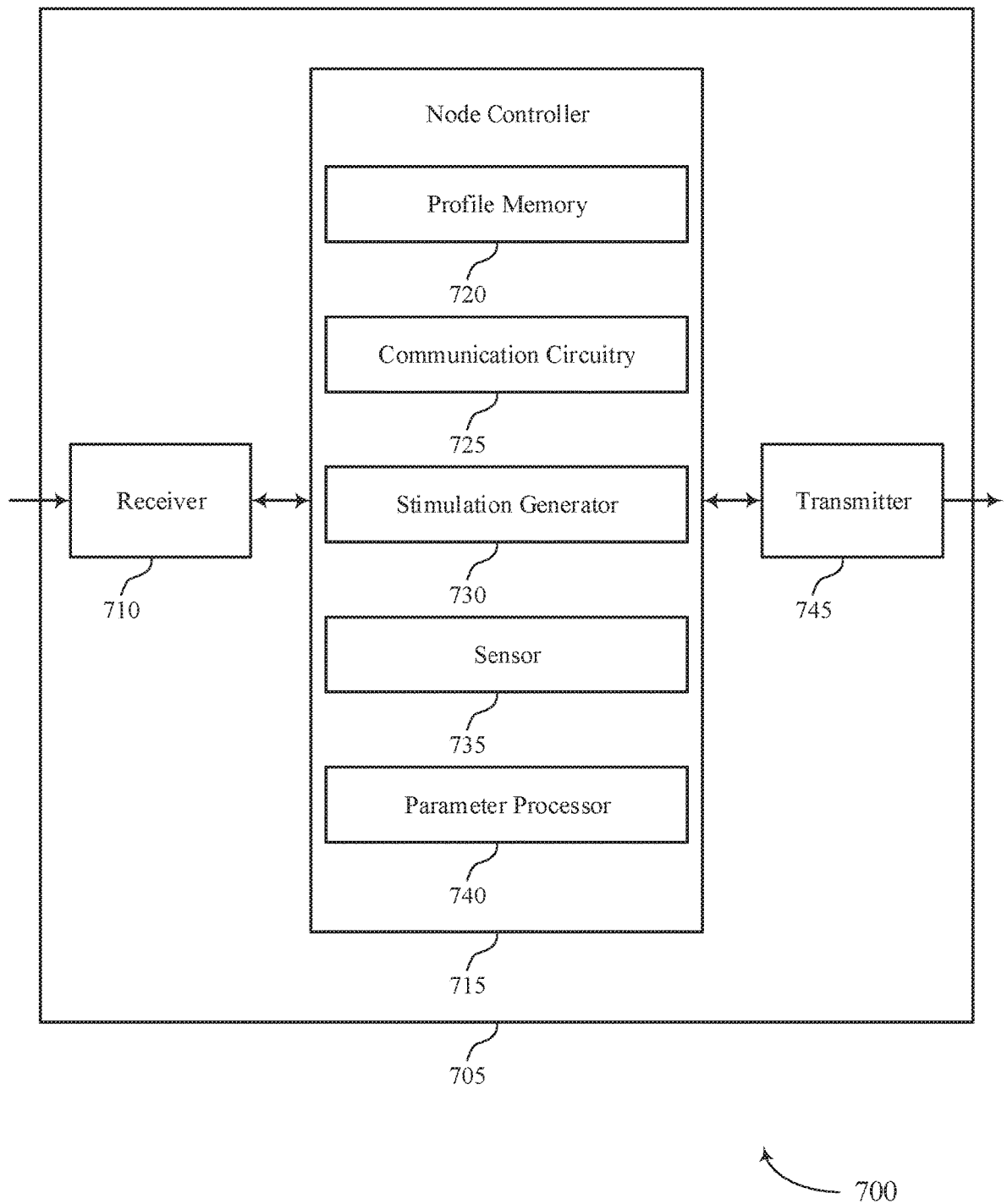

FIG. 7 shows a block diagram 700 of a device 705 that supports implantable stimulation node configuration in accordance with aspects of the present disclosure. The device 705 may be an example of aspects of a device 605 or a device 115 as described herein. The device 705 may include a receiver 710, a node controller 715, and a transmitter 745. The device 705 may also include a processor. Each of these components may be in communication with one another (e.g., via one or more buses).

The receiver 710 may receive information such as packets, user data, or control information associated with various information channels (e.g., control channels, data channels, and information related to implantable stimulation node configuration, etc.). Information may be passed on to other components of the device 705. The receiver 710 may be an example of aspects of the transceiver 920 described with reference to FIG. 9. The receiver 710 may utilize a single antenna or a set of antennas.

The node controller 715 may be an example of aspects of the node controller 615 as described herein. The node controller 715 may include a profile memory 720, a communication circuitry 725, a stimulation generator 730, a sensor 735, and a parameter processor 740. The node controller 715 may be an example of aspects of the node controller 910 described herein.

The profile memory 720 may store a set of stimulation profiles in a memory during a configuration phase. The profile memory 720 may store a set of sensing profiles in a memory based on the received configuration instructions, where each sensing profile of the set of sensing profiles defines a set of data processing parameters.

The communication circuitry 725 may receive a stimulation command corresponding to a stimulation profile of the set of stimulation profiles during a treatment phase. The communication circuitry 725 may receive configuration instructions during a configuration phase. The stimulation generator 730 may deliver stimulation based on the stimulation profile corresponding to the received stimulation command.

The sensor 735 may receive a sensed input during a sensing phase. The parameter processor 740 may transmit a reduced set of the received sensed input based on the set of data processing parameters corresponding to a sensing profile of the set of sensing profiles.

The transmitter 745 may transmit signals generated by other components of the device 705. In some examples, the transmitter 745 may be collocated with a receiver 710 in a transceiver module. For example, the transmitter 745 may be an example of aspects of the transceiver 920 described with reference to FIG. 9. The transmitter 745 may utilize a single antenna or a set of antennas.

Figure 8:
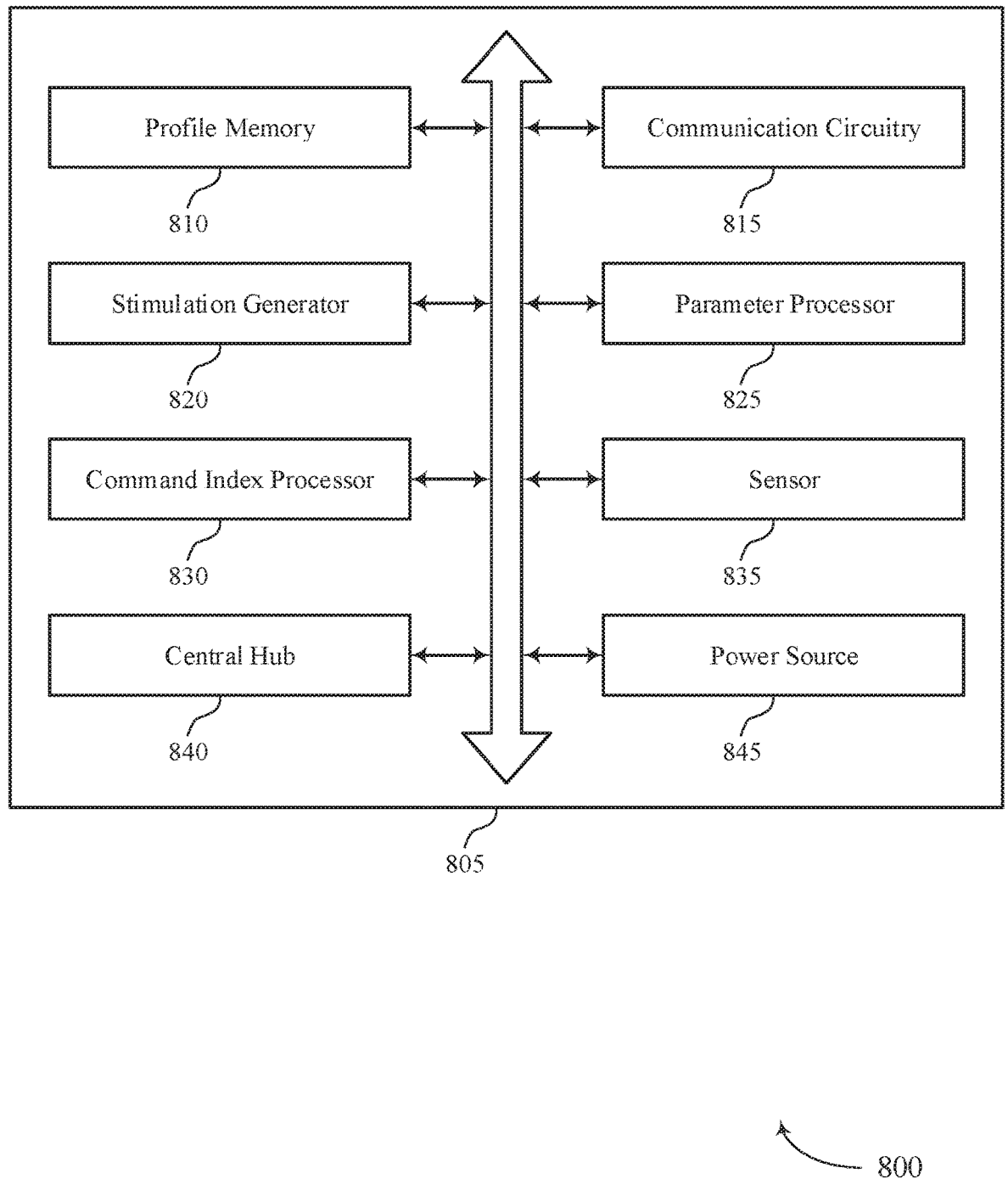
FIG. 8 shows a block diagram of a node controller that supports implantable stimulation node configuration in accordance with aspects of the present disclosure.

FIG. 8 shows a block diagram 800 of a node controller 805 that supports implantable stimulation node configuration in accordance with aspects of the present disclosure. The node controller 805 may be an example of aspects of a node controller 615, a node controller 715, or a node controller 910 described herein. The node controller 805 may include a profile memory 810, a communication circuitry 815, a stimulation generator 820, a parameter processor 825, a command index processor 830, a sensor 835, a central hub 840, and a power source 845. Each of these modules may communicate, directly or indirectly, with one another (e.g., via one or more buses).

The profile memory 810 may store a set of stimulation profiles in a memory during a configuration phase or a first time period. In some cases, the configuration phase includes a first signal transmission timing restriction and the stimulation phase includes a second signal transmission timing restriction that is greater than the first signal transmission timing restriction.

In some cases, the set of stimulation profiles includes generic stimulation profiles and patient specific stimulation profiles. In some cases, the set of stimulation profiles include a lookup table, an algorithm that calculates modulation patterns from sensed inputs, or both. In some examples, the profile memory 810 may store a set of sensing profiles in a memory based on the received configuration instructions, where each sensing profile of the set of sensing profiles defines a set of data processing parameters.

The communication circuitry 815 may receive a stimulation command corresponding to a stimulation profile of the set of stimulation profiles during a treatment phase. In some examples, the communication circuitry 815 may receive a stimulation command from an implantable hub corresponding to a stimulation profile of the set of stimulation profiles during a second time period. In some examples, the communication circuitry 815 may receive configuration instructions during a configuration phase.

In some examples, the communication circuitry 815 may receive an updated stimulation command during the treatment phase based on real-time sensed inputs. In some cases, the real-time sensed inputs change during the treatment phase. In some examples, the communication circuitry 815 may communicate signals over a limited bandwidth on communication circuitry, where the limited bandwidth is based on the implantable stimulation node being implanted in a body.

In some cases, the second signal transmission timing restriction is based at least in part a feedback timing restriction corresponding to the delivered stimulation. In some cases, the implantable hub is electrically coupled with the set of implantable stimulation nodes via a wired connection. The wired connection may be used for communication between devices and/or for static or dynamic power control of the stimulation nodes.

The stimulation generator 820 may deliver stimulation based on the stimulation profile corresponding to the received stimulation command. In some examples, the stimulation generator 820 may deliver an updated stimulation within the treatment phase based on a stimulation profile corresponding to the updated stimulation command. In some cases, the stimulation mode may require frequent refresh of statically enabled profiles during the treatment phase, for example, to prevent unintended stimulation if communication between remote devices is interrupted.

In some cases, the implantable stimulation node includes a set of electrodes. In some cases, at least one electrode of the set of electrodes delivers stimulation according to the stimulation profile corresponding to the received stimulation command. In some cases, the stimulation node is configured to be implanted into a human body.

The parameter processor 825 may transmit a reduced set of the received sensed input based on the set of data processing parameters corresponding to a sensing profile of the set of sensing profiles. In some examples, the parameter processor 825 may identify a first set of stimulation parameters based on the stimulation profile corresponding to the received stimulation command. In some examples, the parameter processor 825 may identify a second set of stimulation parameters directly from the received stimulation command, where the stimulation is delivered based on the first set of stimulation parameters and the second set of stimulation parameters.

In some examples, the parameter processor 825 may reduce the received sensed input to the reduced set of the received sensed input by applying the set of data processing parameters corresponding to the sensing profile of the set of sensing profiles. In some cases, the reducing is based on an available bandwidth, a timing constraint, a pre-configuration, or a combination thereof. The command index processor 830 may identify an index of the stimulation command, where the index is associated with the stimulation profile of the set of stimulation profiles.

The sensor 835 may receive a sensed input during a sensing phase. In some examples, the sensor 835 may detect, by a sensing device, real-time sensed inputs. In some examples, the sensor 835 may transmit, by the sensing device, the real-time sensed inputs to the implantable hub, where the sensing device is configured to be coupled with a human body. In some cases, the sensing device includes a prosthetic, a wearable device, a therapy device, or a combination thereof.

The central hub 840 may determine, at the implantable hub, the stimulation command corresponding to the stimulation profile based on the real-time sensed inputs received from the sensing device. In some examples, the central hub 840 may transmit the stimulation command to one or more of the set of implantable stimulation nodes. In some cases, the implantable hub is configured to wirelessly communicate with an external device.

The power source 845 may provide power to the device. In some cases, the implantable hub includes a battery source configured to provide power to the set of implantable stimulation nodes.

Figure 9:
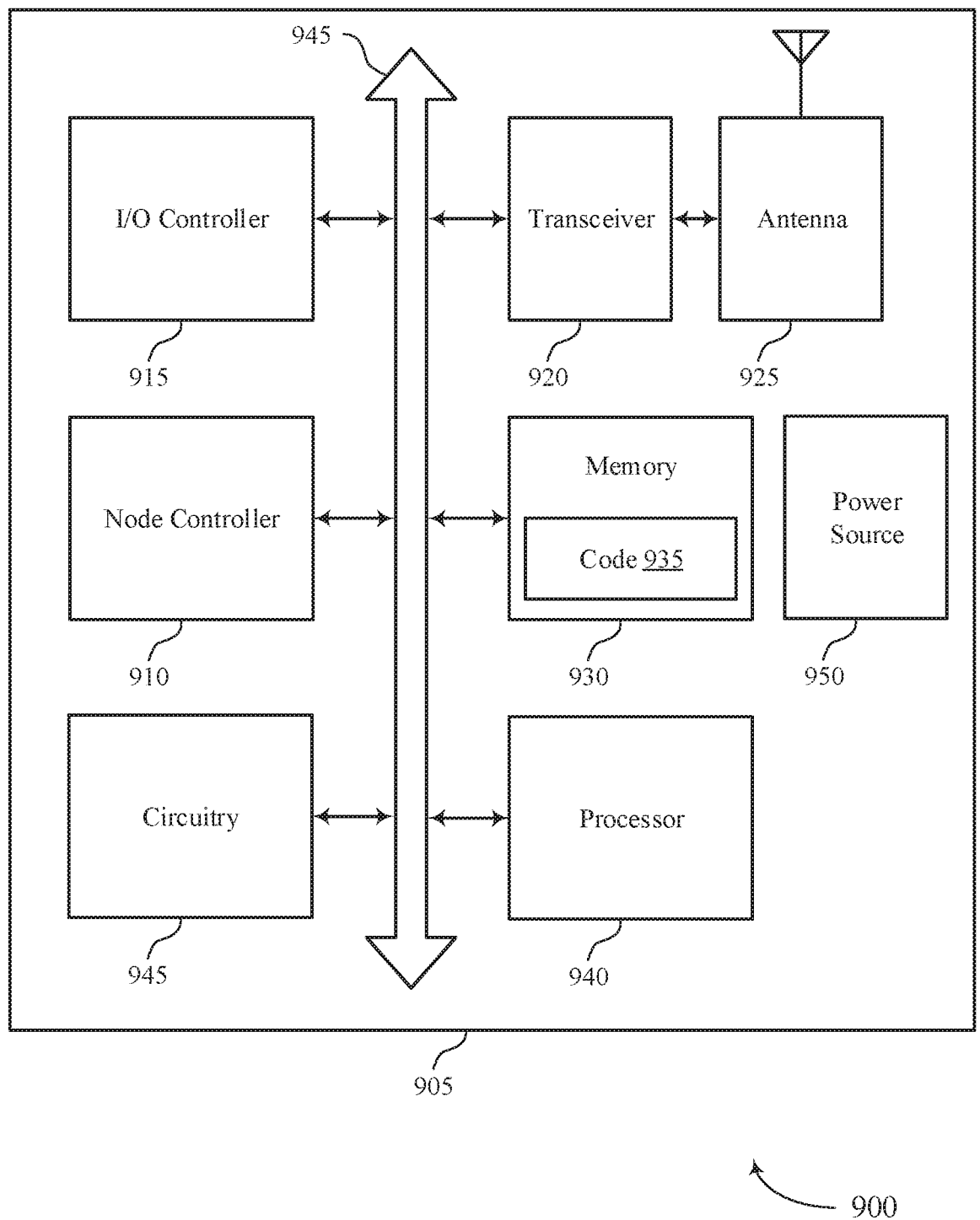
FIG. 9 shows a diagram of a system including a device that supports implantable stimulation node configuration in accordance with aspects of the present disclosure.

FIG. 9 shows a diagram of a system 900 including a device 905 that supports implantable stimulation node configuration in accordance with aspects of the present disclosure. The device 905 may be an example of or include the components of device 605, device 705, or a device as described herein. The device 905 may include components for bi-directional voice and data communications including components for transmitting and receiving communications, including a node controller 910, an I/O controller 915, a transceiver 920, an antenna 925, memory 930, and a processor 940. These components may be in electronic communication via one or more buses (e.g., bus 945).

The node controller 910 may store a set of stimulation profiles in a memory during a configuration phase, receive a stimulation command corresponding to a stimulation profile of the set of stimulation profiles during a treatment phase, and deliver stimulation based on the stimulation profile corresponding to the received stimulation command. The node controller 910 may also store a set of stimulation profiles in a memory during a first time period, receive a stimulation command from an implantable hub corresponding to a stimulation profile of the set of stimulation profiles during a second time period, and deliver stimulation based on the stimulation profile corresponding to the received stimulation command. The node controller 910 may also transmit status information in response to stimulation profile updates that report the operational status (e.g. regulation status or loading) the device 905 (e.g., stimulation node). The node controller 910 may also receive configuration instructions during a configuration phase, store a set of sensing profiles in a memory based on the received configuration instructions, where each sensing profile of the set of sensing profiles defines a set of data processing parameters, receive a sensed input during a sensing phase, and transmit a reduced set of the received sensed input based on the set of data processing parameters corresponding to a sensing profile of the set of sensing profiles.

The I/O controller 915 may manage input and output signals for the device 905. The I/O controller 915 may also manage peripherals not integrated into the device 905. In some cases, the I/O controller 915 may represent a physical connection or port to an external peripheral. In some cases, the I/O controller 915 may utilize an operating system such as iOS®, ANDROID®, MS-DOS®, MS-WINDOWS®, OS/2®, UNIX®, LINUX®, or another known operating system. In other cases, the I/O controller 915 may represent or interact with a modem, a keyboard, a mouse, a touchscreen, or a similar device. In some cases, the I/O controller 915 may be implemented as part of a processor. In some cases, a user may interact with the device 905 via the I/O controller 915 or via hardware components controlled by the I/O controller 915.

The transceiver 920 may communicate bi-directionally, via one or more antennas, wired, or wireless links as described above. For example, the transceiver 920 may represent a wireless transceiver and may communicate bi-directionally with another wireless transceiver. The transceiver 920 may also include a modem to modulate the packets and provide the modulated packets to the antennas for transmission, and to demodulate packets received from the antennas.

In some cases, the wireless device may include a single antenna 925. However, in some cases the device may have more than one antenna 925, which may be capable of concurrently transmitting or receiving multiple wireless transmissions.

The memory 930 may include RAM and ROM. The memory 930 may store computer-readable, computer-executable code 935 including instructions that, when executed, cause the processor to perform various functions described herein. In some cases, the memory 930 may contain, among other things, a BIOS which may control basic hardware or software operation such as the interaction with peripheral components or devices.

The processor 940 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof).

In some cases, the processor 940 may be configured to operate a memory array using a memory controller. In other cases, a memory controller may be integrated into the processor 940. The processor 940 may be configured to execute computer-readable instructions stored in a memory (e.g., the memory 930) to cause the device 905 to perform various functions (e.g., functions or tasks supporting implantable stimulation node configuration).

The code 935 may include instructions to implement aspects of the present disclosure, including instructions to support implantable node configuration. The code 935 may be stored in a non-transitory computer-readable medium such as system memory or other type of memory. In some cases, the code 935 may not be directly executable by the processor 940 but may cause a computer (e.g., when compiled and executed) to perform functions described herein.

Circuitry 945 may allow communication between devices. The circuitry may transfer both data and power (e.g., from power source 950) between components. In some examples, the circuitry 945 may be a switch array, switch matrix, multiplexer, or any other type of switching circuitry configured to selectively supply stimulation energy to selected electrodes of stimulation nodes and to sense bioelectrical neural signals at a sensing node.

Figure 10:
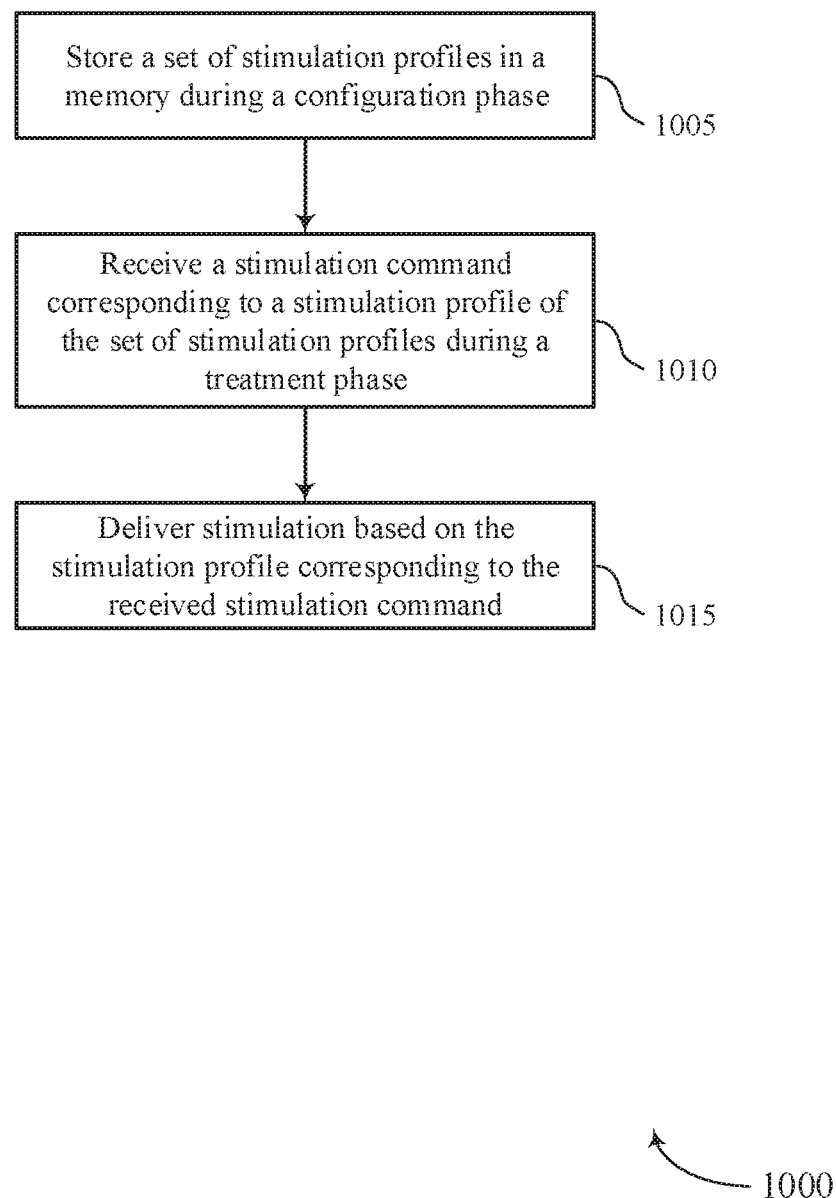
FIGS. 10 through 15 show flowcharts illustrating methods that support implantable stimulation node configuration in accordance with aspects of the present disclosure.

FIG. 10 shows a flowchart illustrating a method 1000 that supports implantable stimulation node configuration in accordance with aspects of the present disclosure. The operations of method 1000 may be implemented by a device or its components as described herein. For example, the operations of method 1000 may be performed by a node controller as described with reference to FIGS. 6 through 9. In some examples, a device may execute a set of instructions to control the functional elements of the device to perform the functions described below. Additionally or alternatively, a device may perform aspects of the functions described below using special-purpose hardware.

At 1005, the device may store a set of stimulation profiles in a memory during a configuration phase. The operations of 1005 may be performed according to the methods described herein. In some examples, aspects of the operations of 1005 may be performed by a profile memory as described with reference to FIGS. 6 through 9.

At 1010, the device may receive a stimulation command corresponding to a stimulation profile of the set of stimulation profiles during a treatment phase. The operations of 1010 may be performed according to the methods described herein. In some examples, aspects of the operations of 1010 may be performed by a communication circuitry as described with reference to FIGS. 6 through 9.

At 1015, the device may deliver stimulation based on the stimulation profile corresponding to the received stimulation command. The operations of 1015 may be performed according to the methods described herein. In some examples, aspects of the operations of 1015 may be performed by a stimulation generator as described with reference to FIGS. 6 through 9.

Figure 11:
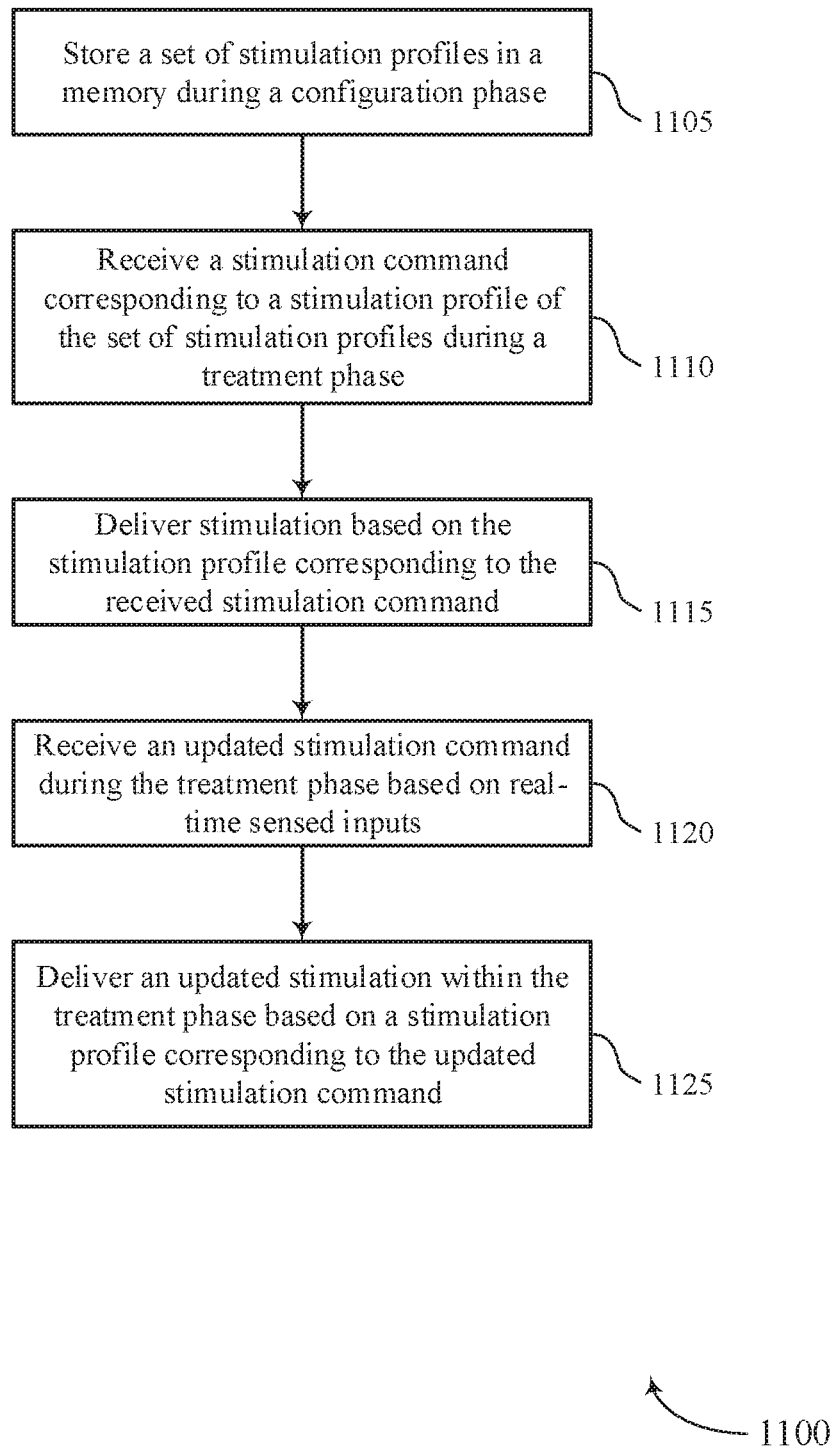

FIG. 11 shows a flowchart illustrating a method 1100 that supports implantable stimulation node configuration in accordance with aspects of the present disclosure. The operations of method 1100 may be implemented by a device or its components as described herein. For example, the operations of method 1100 may be performed by a node controller as described with reference to FIGS. 6 through 9. In some examples, a device may execute a set of instructions to control the functional elements of the device to perform the functions described below. Additionally or alternatively, a device may perform aspects of the functions described below using special-purpose hardware.

At 1105, the device may store a set of stimulation profiles in a memory during a configuration phase. The operations of 1105 may be performed according to the methods described herein. In some examples, aspects of the operations of 1105 may be performed by a profile memory as described with reference to FIGS. 6 through 9.

At 1110, the device may receive a stimulation command corresponding to a stimulation profile of the set of stimulation profiles during a treatment phase. The operations of 1110 may be performed according to the methods described herein. In some examples, aspects of the operations of 1110 may be performed by a communication circuitry as described with reference to FIGS. 6 through 9.

At 1115, the device may deliver stimulation based on the stimulation profile corresponding to the received stimulation command. The operations of 1115 may be performed according to the methods described herein. In some examples, aspects of the operations of 1115 may be performed by a stimulation generator as described with reference to FIGS. 6 through 9.

At 1120, the device may receive an updated stimulation command during the treatment phase based on real-time sensed inputs. The operations of 1120 may be performed according to the methods described herein. In some examples, aspects of the operations of 1120 may be performed by a communication circuitry as described with reference to FIGS. 6 through 9.

At 1125, the device may deliver an updated stimulation within the treatment phase based on a stimulation profile corresponding to the updated stimulation command. The operations of 1125 may be performed according to the methods described herein. In some examples, aspects of the operations of 1125 may be performed by a stimulation generator as described with reference to FIGS. 6 through 9.

Figure 12:
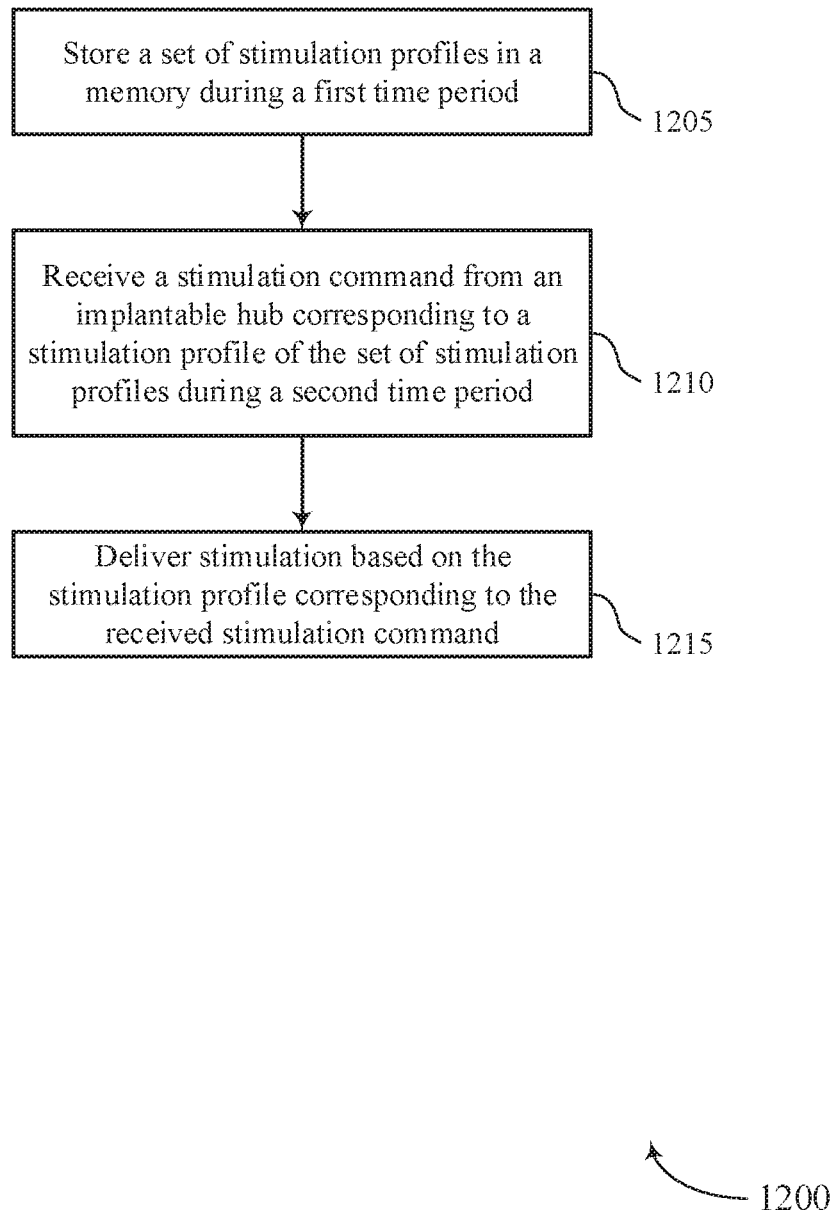

FIG. 12 shows a flowchart illustrating a method 1200 that supports implantable stimulation node configuration in accordance with aspects of the present disclosure. The operations of method 1200 may be implemented by a device or its components as described herein. For example, the operations of method 1200 may be performed by a node controller as described with reference to FIGS. 6 through 9. In some examples, a device may execute a set of instructions to control the functional elements of the device to perform the functions described below. Additionally or alternatively, a device may perform aspects of the functions described below using special-purpose hardware.

At 1205, the device may store a set of stimulation profiles in a memory during a first time period. The operations of 1205 may be performed according to the methods described herein. In some examples, aspects of the operations of 1205 may be performed by a profile memory as described with reference to FIGS. 6 through 9.

At 1210, the device may receive a stimulation command from an implantable hub corresponding to a stimulation profile of the set of stimulation profiles during a second time period. The operations of 1210 may be performed according to the methods described herein. In some examples, aspects of the operations of 1210 may be performed by a communication circuitry as described with reference to FIGS. 6 through 9.

At 1215, the device may deliver stimulation based on the stimulation profile corresponding to the received stimulation command. The operations of 1215 may be performed according to the methods described herein. In some examples, aspects of the operations of 1215 may be performed by a stimulation generator as described with reference to FIGS. 6 through 9.

Figure 13:
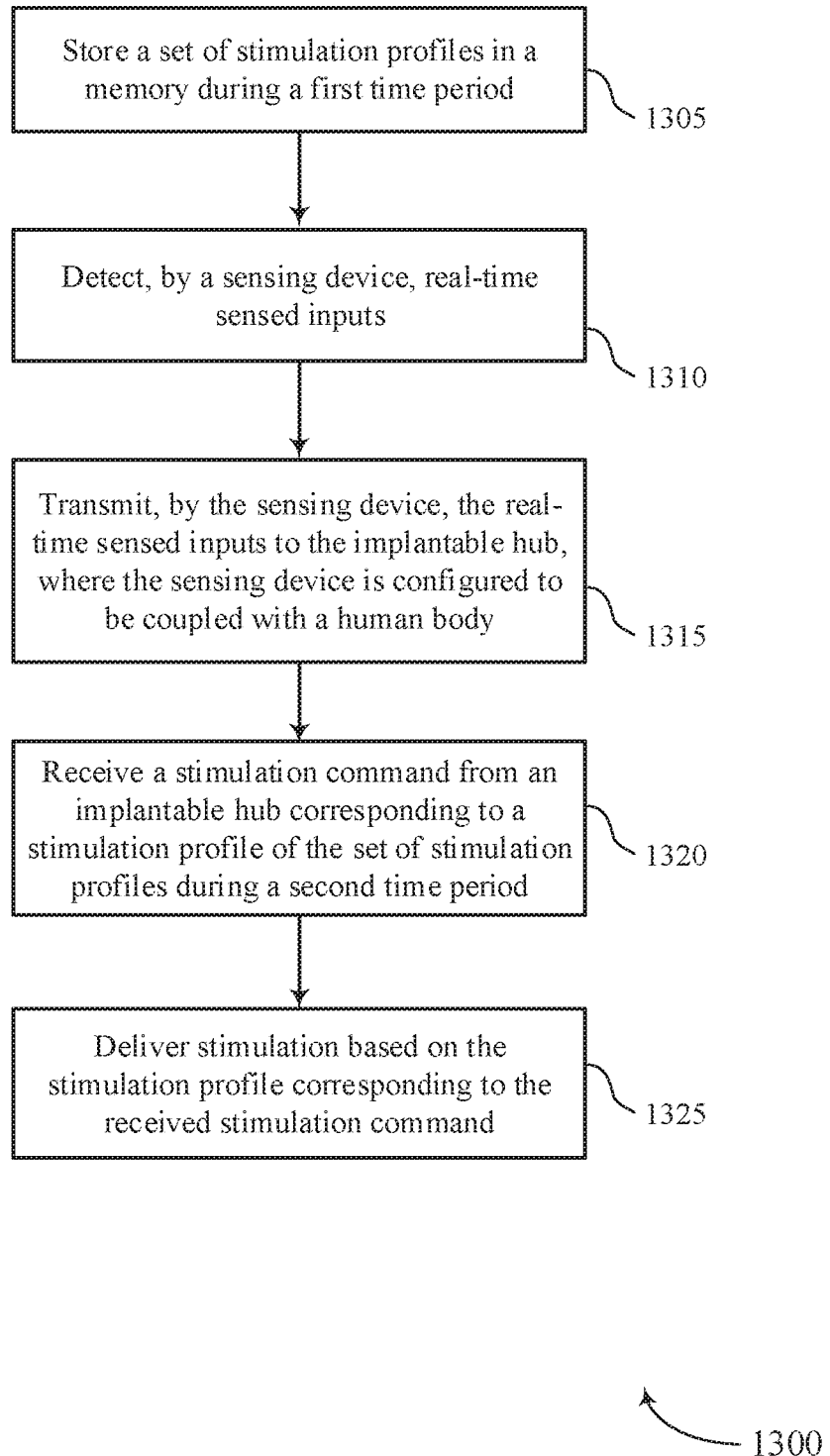

FIG. 13 shows a flowchart illustrating a method 1300 that supports implantable stimulation node configuration in accordance with aspects of the present disclosure. The operations of method 1300 may be implemented by a device or its components as described herein. For example, the operations of method 1300 may be performed by a node controller as described with reference to FIGS. 6 through 9. In some examples, a device may execute a set of instructions to control the functional elements of the device to perform the functions described below. Additionally or alternatively, a device may perform aspects of the functions described below using special-purpose hardware.

At 1305, the device may store a set of stimulation profiles in a memory during a first time period. The operations of 1305 may be performed according to the methods described herein. In some examples, aspects of the operations of 1305 may be performed by a profile memory as described with reference to FIGS. 6 through 9.

At 1310, the device may detect, by a sensing device, real-time sensed inputs. The operations of 1310 may be performed according to the methods described herein. In some examples, aspects of the operations of 1310 may be performed by a sensor as described with reference to FIGS. 6 through 9.

At 1315, the device may transmit, by the sensing device, the real-time sensed inputs to the implantable hub, where the sensing device is configured to be coupled with a human body. The operations of 1315 may be performed according to the methods described herein. In some examples, aspects of the operations of 1315 may be performed by a sensor as described with reference to FIGS. 6 through 9.

At 1320, the device may receive a stimulation command from an implantable hub corresponding to a stimulation profile of the set of stimulation profiles during a second time period. The operations of 1320 may be performed according to the methods described herein. In some examples, aspects of the operations of 1320 may be performed by a communication circuitry as described with reference to FIGS. 6 through 9.

At 1325, the device may deliver stimulation based on the stimulation profile corresponding to the received stimulation command. The operations of 1325 may be performed according to the methods described herein. In some examples, aspects of the operations of 1325 may be performed by a stimulation generator as described with reference to FIGS. 6 through 9.

Figure 14:
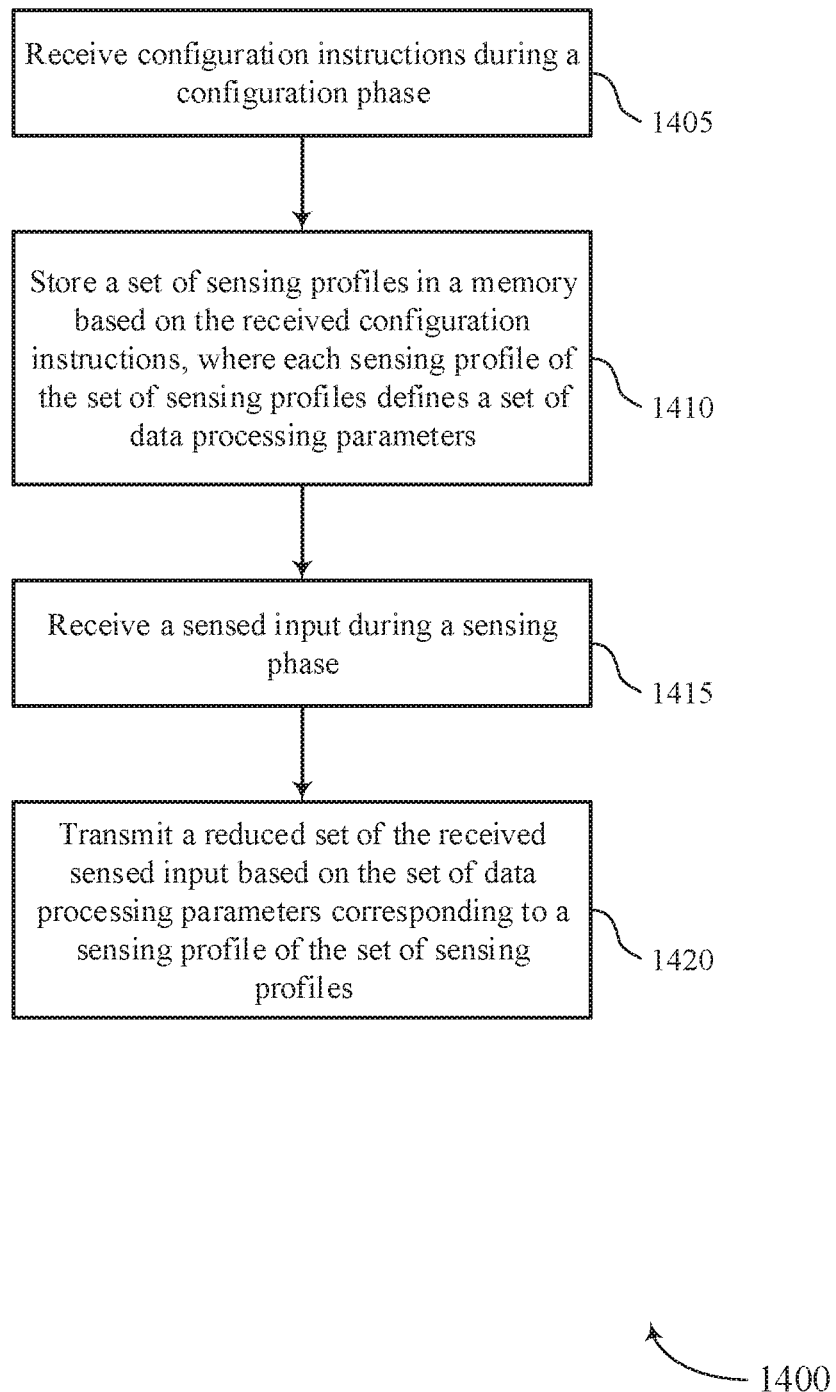

FIG. 14 shows a flowchart illustrating a method 1400 that supports implantable stimulation node configuration in accordance with aspects of the present disclosure. The operations of method 1400 may be implemented by a device or its components as described herein. For example, the operations of method 1400 may be performed by a node controller as described with reference to FIGS. 6 through 9. In some examples, a device may execute a set of instructions to control the functional elements of the device to perform the functions described below. Additionally or alternatively, a device may perform aspects of the functions described below using special-purpose hardware.

At 1405, the device may receive configuration instructions during a configuration phase. The operations of 1405 may be performed according to the methods described herein. In some examples, aspects of the operations of 1405 may be performed by a communication circuitry as described with reference to FIGS. 6 through 9.

At 1410, the device may store a set of sensing profiles in a memory based on the received configuration instructions, where each sensing profile of the set of sensing profiles defines a set of data processing parameters. The operations of 1410 may be performed according to the methods described herein. In some examples, aspects of the operations of 1410 may be performed by a profile memory as described with reference to FIGS. 6 through 9.

At 1415, the device may receive a sensed input during a sensing phase. The operations of 1415 may be performed according to the methods described herein. In some examples, aspects of the operations of 1415 may be performed by a sensor as described with reference to FIGS. 6 through 9.

At 1420, the device may transmit a reduced set of the received sensed input based on the set of data processing parameters corresponding to a sensing profile of the set of sensing profiles. The operations of 1420 may be performed according to the methods described herein. In some examples, aspects of the operations of 1420 may be performed by a parameter processor as described with reference to FIGS. 6 through 9.

Figure 15:
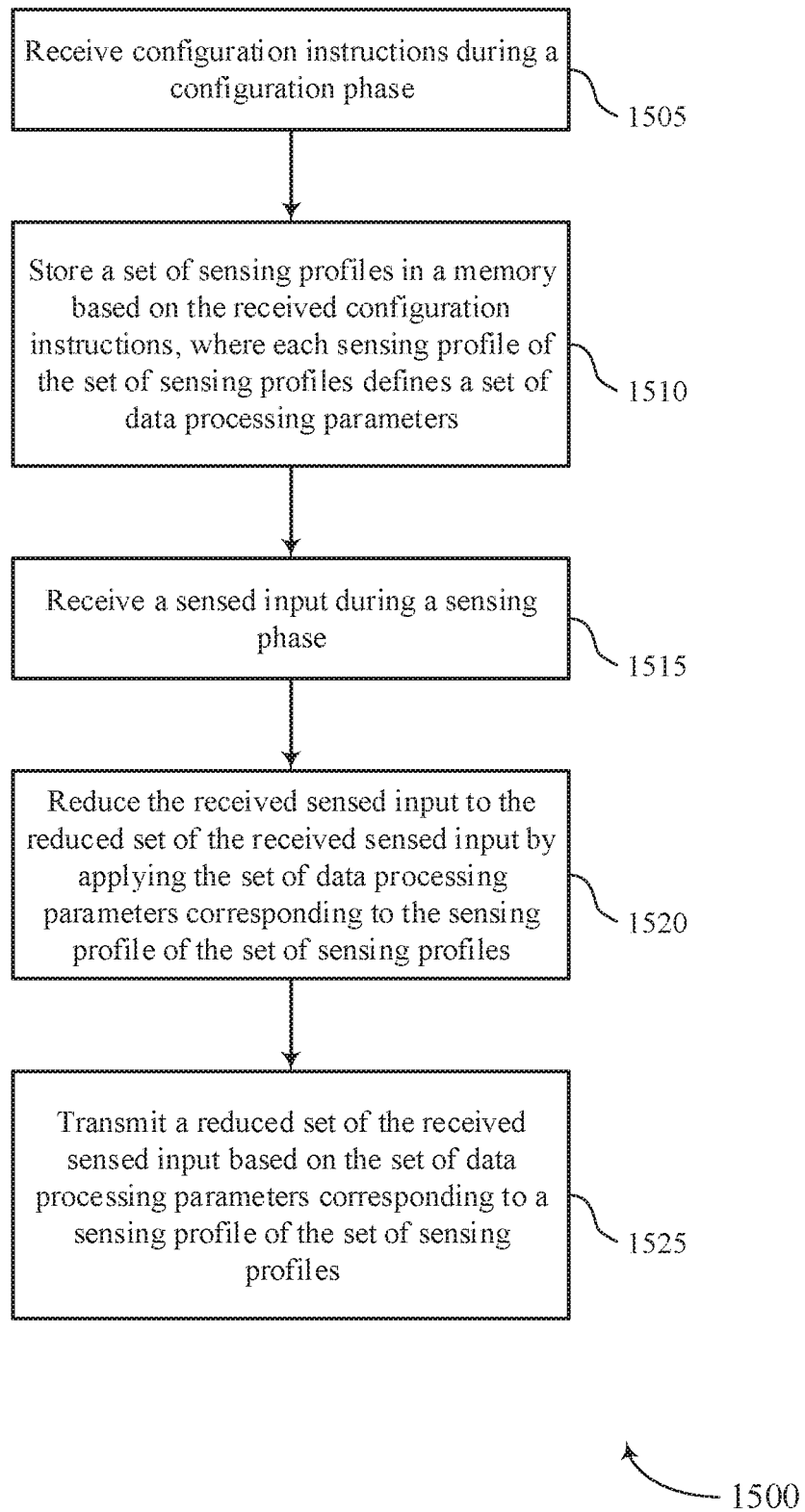

FIG. 15 shows a flowchart illustrating a method 1500 that supports implantable stimulation node configuration in accordance with aspects of the present disclosure. The operations of method 1500 may be implemented by a device or its components as described herein. For example, the operations of method 1500 may be performed by a node controller as described with reference to FIGS. 6 through 9. In some examples, a device may execute a set of instructions to control the functional elements of the device to perform the functions described below. Additionally or alternatively, a device may perform aspects of the functions described below using special-purpose hardware.

At 1505, the device may receive configuration instructions during a configuration phase. The operations of 1505 may be performed according to the methods described herein. In some examples, aspects of the operations of 1505 may be performed by a communication circuitry as described with reference to FIGS. 6 through 9.

At 1510, the device may store a set of sensing profiles in a memory based on the received configuration instructions, where each sensing profile of the set of sensing profiles defines a set of data processing parameters. The operations of 1510 may be performed according to the methods described herein. In some examples, aspects of the operations of 1510 may be performed by a profile memory as described with reference to FIGS. 6 through 9.

At 1515, the device may receive a sensed input during a sensing phase. The operations of 1515 may be performed according to the methods described herein. In some examples, aspects of the operations of 1515 may be performed by a sensor as described with reference to FIGS. 6 through 9.

At 1520, the device may reduce the received sensed input to the reduced set of the received sensed input by applying the set of data processing parameters corresponding to the sensing profile of the set of sensing profiles. The operations of 1520 may be performed according to the methods described herein. In some examples, aspects of the operations of 1520 may be performed by a parameter processor as described with reference to FIGS. 6 through 9.

At 1525, the device may transmit a reduced set of the received sensed input based on the set of data processing parameters corresponding to a sensing profile of the set of sensing profiles. The operations of 1525 may be performed according to the methods described herein. In some examples, aspects of the operations of 1525 may be performed by a parameter processor as described with reference to FIGS. 6 through 9.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an ASIC, a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). A processor may in some cases be in electronic communication with a memory, where the memory stores instructions that are executable by the processor. Thus, the functions described herein may be performed by one or more other processing units (or cores), on at least one integrated circuit (IC). In various examples, different types of ICs may be used (e.g., Structured/Platform ASICs, an FPGA, or another semi-custom IC), which may be programmed in any manner known in the art. The functions of each unit may also be implemented, in whole or in part, with instructions embodied in a memory, formatted to be executed by one or more general or application-specific processors.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims. "or" as used in a list of items (for example, a list of items prefaced by a phrase such as "at least one of" or "one or more of") indicates an inclusive list such that, for example, a list of at least one of A. B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media may comprise RAM, ROM, electrically erasable programmable read only memory (EEPROM), compact disk (CD) ROM or other optical disk storage, magnetic disk storage or other magnetic storage devices, or any other non-transitory medium that may be used to carry or store desired program code means in the form of instructions or data structures and that may be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. An implantable stimulation node, comprising:
   a processor;

memory in electronic communication with the processor; and instructions stored in the memory and operable, when executed by the processor, to cause the stimulation node to:
store, at the stimulation node, a set of stimulation profiles in the memory during a configuration phase;
receive, at the stimulation node, a stimulation command comprising an index pointing to which stimulation profile of the set of stimulation profiles to use during a treatment phase, wherein a data size of the index is smaller than a data size of the stimulation profile;
deliver, at the stimulation node and during the treatment phase, stimulation based at least in part on the stimulation profile corresponding to the received stimulation command;
receive, during the treatment phase and after delivering the stimulation, real-time sensed inputs that change during the treatment phase;
receive, during the treatment phase, an updated stimulation command comprising a different index pointing to a different stimulation profile of the set of stimulation profiles based at least in part on the received real-time sensed inputs that change during the treatment phase, wherein a data size of the different index is smaller than a data size of the different stimulation profile; and
deliver, during the treatment phase, an updated stimulation based at least in part on the different stimulation profile corresponding to the updated stimulation command.

2. The implantable stimulation node of claim 1, further comprising:
communication circuitry configured for communicating signals over a limited bandwidth, wherein the limited bandwidth is based at least in part on the implantable stimulation node being implanted in a body.

3. The implantable stimulation node of claim 1, wherein the set of stimulation profiles comprises generic stimulation profiles and patient specific stimulation profiles.

4. The implantable stimulation node of claim 1, wherein the configuration phase comprises a first signal transmission timing restriction and the treatment phase comprises a second signal transmission timing restriction that is greater than the first signal transmission timing restriction.

5. The implantable stimulation node of claim 4, wherein the second signal transmission timing restriction is based at least in part on a feedback timing restriction corresponding to the delivered stimulation.

6. The implantable stimulation node of claim 1, further comprising:
a plurality of electrodes.

7. The implantable stimulation node of claim 6, wherein at least one electrode of the plurality of electrodes delivers stimulation according to the stimulation profile corresponding to the received stimulation command.

8. The implantable stimulation node of claim 1, wherein the set of stimulation profiles comprise a lookup table, an algorithm that calculates modulation patterns from sensed inputs, or both.

9. The implantable stimulation node of claim 1, wherein the instructions are operable to cause the stimulation node to:
identify a first set of stimulation parameters based at least in part on the stimulation profile corresponding to the received stimulation command; and identify a second set of stimulation parameters directly from the received stimulation command, wherein the stimulation is delivered based at least in part on the first set of stimulation parameters and the second set of stimulation parameters.

10. The implantable stimulation node of claim 1, wherein the instructions are operable to cause the stimulation node to:
identify the index of the stimulation command, wherein the index is associated with the stimulation profile of the set of stimulation profiles.

11. The implantable stimulation node of claim 1, wherein the stimulation node is configured to be implanted into a human body.

12. An implantable stimulation system, comprising:
an implantable hub; and
a plurality of implantable stimulation nodes, each implantable stimulation node comprising:
a processor;
memory in electronic communication with the processor; and
instructions stored in the memory and operable, when executed by the processor, to cause the stimulation node to:
store, at the stimulation node, a set of stimulation profiles in the memory during a first time period;
receive, at the stimulation node, a stimulation command from the implantable hub comprising an index pointing to which stimulation profile of the set of stimulation profiles to use during a second time period, wherein a data size of the index is smaller than a data size of the stimulation profile;
deliver, at the stimulation node and during the second time period, stimulation based at least in part on the stimulation profile corresponding to the received stimulation command;
receive, during the second time period and after delivering the stimulation, real-time sensed inputs that change during the second time period;
receive, during the second time period, an updated stimulation command comprising a different index pointing to a different stimulation profile of the set of stimulation profiles based at least in part on the received real-time sensed inputs that change during the second time period, wherein a data size of the different index is smaller than a data size of the different stimulation profile; and
deliver, during the second time period, an updated stimulation based at least in part on the different stimulation profile corresponding to the updated stimulation command.

13. The implantable stimulation system of claim 12, further comprising:
a sensing device configured to be coupled with a human body and configured to detect and transmit the real-time sensed inputs to the implantable hub.

14. The implantable stimulation system of claim 13, wherein the implantable hub is configured to determine the stimulation command corresponding to the stimulation profile based at least in part on the real-time sensed inputs received from the sensing device, and is further configured to transmit the stimulation command to one or more of the plurality of implantable stimulation nodes.

15. The implantable stimulation system of claim 13, wherein the sensing device comprises a prosthetic, a wearable device, a therapy device, or a combination thereof.

16. The implantable stimulation system of claim 12, wherein the implantable hub comprises a battery source configured to provide power to the plurality of implantable stimulation nodes.

17. The implantable stimulation system of claim 12, wherein the implantable hub is configured to wirelessly communicate with an external device.

18. The implantable stimulation system of claim 12, wherein the implantable hub is electrically coupled with the plurality of implantable stimulation nodes via a wired connection.

* * * * *